(12) United States Patent
Lee et al.

(10) Patent No.: US 10,306,017 B2
(45) Date of Patent: May 28, 2019

(54) WEAR SYSTEM AND METHOD FOR PROVIDING SERVICE

(71) Applicant: SAMSUNG ELECTRONICS CO., LTD., Suwon-si, Gyeonggi-do (KR)

(72) Inventors: Yu-Won Lee, Suwon-si (KR); Young-Hoon Kim, Seongnam-si (KR); Hee-Jun Song, Suwon-si (KR); Il-Hwan Choi, Yongin-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 145 days.

(21) Appl. No.: 15/360,114

(22) Filed: Nov. 23, 2016

(65) Prior Publication Data

US 2017/0149933 A1    May 25, 2017

(30) Foreign Application Priority Data

Nov. 24, 2015  (KR) .................... 10-2015-0164937

(51) Int. Cl.
*H04L 29/08* (2006.01)
*H04L 29/06* (2006.01)
(Continued)

(52) U.S. Cl.
CPC .......... *H04L 67/327* (2013.01); *A61B 5/0205* (2013.01); *A61B 5/117* (2013.01);
(Continued)

(58) Field of Classification Search
CPC ..... H04B 1/385; H04L 67/306; H04L 67/327; H04L 67/42; H04L 63/0853; H04W 12/06;
(Continued)

(56) References Cited

U.S. PATENT DOCUMENTS 7,853,475 B2    12/2010  Deaton et al.
2008/0216171 A1  9/2008  Sano et al.
(Continued)

FOREIGN PATENT DOCUMENTS

JP    2008-198028    8/2008
JP    2011-081756    4/2011
(Continued)

OTHER PUBLICATIONS

Search Report and Written Opinion dated Jan. 20, 2017 in counterpart International Patent Application No. PCT/KR2016/013532.

*Primary Examiner* — Shean Tokuta
*Assistant Examiner* — Juan C Turriate Gastulo
(74) *Attorney, Agent, or Firm* — Nixon & Vanderhye P.C.

(57) ABSTRACT

The present disclosure provides a wear system for providing a service. The wear system may comprise a wear device configured to detect authentication information regarding a user wearing the wear device in a first state, to transmit the authentication information to a server, and if authentication of the user is complete through the server, to detect user data of the wear device in a second state and to transmit the user data to the server and the server, upon detecting identification information regarding the user using the authentication information received from the wear device, to complete the authentication of the user, to generate a user profile based on the user data received from the wear device, to store the user profile corresponding to the identification information, and to provide service information related to the user to the wear device.

13 Claims, 24 Drawing Sheets

(51) Int. Cl.
| | |
|---|---|
| *H04B 1/3827* | (2015.01) |
| *H04W 12/06* | (2009.01) |
| *H04W 12/08* | (2009.01) |
| *A61B 5/0205* | (2006.01) |
| *A61B 5/117* | (2016.01) |
| *A61B 5/00* | (2006.01) |
| *A61B 5/04* | (2006.01) |
| *A61B 5/11* | (2006.01) |

(52) U.S. Cl.
CPC ........... *A61B 5/6801* (2013.01); *H04B 1/385* (2013.01); *H04L 63/0853* (2013.01); *H04L 67/306* (2013.01); *H04L 67/42* (2013.01); *H04W 12/06* (2013.01); *H04W 12/08* (2013.01); *A61B 5/00* (2013.01); *A61B 5/04* (2013.01); *A61B 5/11* (2013.01); *A61B 2560/0209* (2013.01)

(58) Field of Classification Search
CPC . H04W 12/08; A61B 5/00; A61B 5/04; A61B 5/0205; A61B 5/11; A61B 5/117; A61B 5/6801; A61B 2560/0209
See application file for complete search history.

(56) References Cited

U.S. PATENT DOCUMENTS

| | | | |
|---|---|---|---|
| 2012/0086550 A1* | 4/2012 | LeBlanc | A61B 5/1038 340/5.82 |
| 2014/0009258 A1 | 1/2014 | Case, Jr. | |
| 2014/0163704 A1 | 6/2014 | DePietro et al. | |
| 2014/0199672 A1 | 7/2014 | Davidson | |
| 2014/0320307 A1* | 10/2014 | Matsuno | A61B 5/0002 340/870.07 |
| 2015/0342524 A1* | 12/2015 | Sudo | G06F 21/35 340/870.07 |
| 2016/0004224 A1* | 1/2016 | Pi | G04G 21/025 368/10 |
| 2016/0191511 A1* | 6/2016 | Tijerina | H04L 63/0853 726/7 |

FOREIGN PATENT DOCUMENTS

| | | |
|---|---|---|
| KR | 10-1040674 | 6/2011 |
| KR | 10-2013-0006387 | 1/2013 |
| KR | 10-2013-0040111 | 4/2013 |
| KR | 10-1472502 | 12/2014 |
| WO | 2009/054554 | 4/2009 |
| WO | 2014/028765 | 2/2014 |

* cited by examiner

| | 810 | 820a | 820b | 820c |
|---|---|---|---|---|
| | IDENTIFICATION INFORMATION (GUID) | ECG | HEARTBEAT WAVEFORM | FINGERPRINT |
| 810a | AABCDX1E | 0101020030404 | | 23876572371 |
| 810b | 1DC89AXC | | 328468921012 | |
| 810c | 91aXCG3F | | 681821381906 | 128236757192 |

FIG.8

| | SERVICE TYPE (INFORMATION) | SENSORS REQUIRED | HW SPECIFICATIONS REQUIRED |
|---|---|---|---|
| 1401a | ADVERTISEMENT | TOUCH, ECG, EMG, HEARTBEAT | 2GB RAM, Display |
| 1401b | Personalized Fitness | ACCELERATION, EMG, ECG | 2GB RAM |

FIG.14

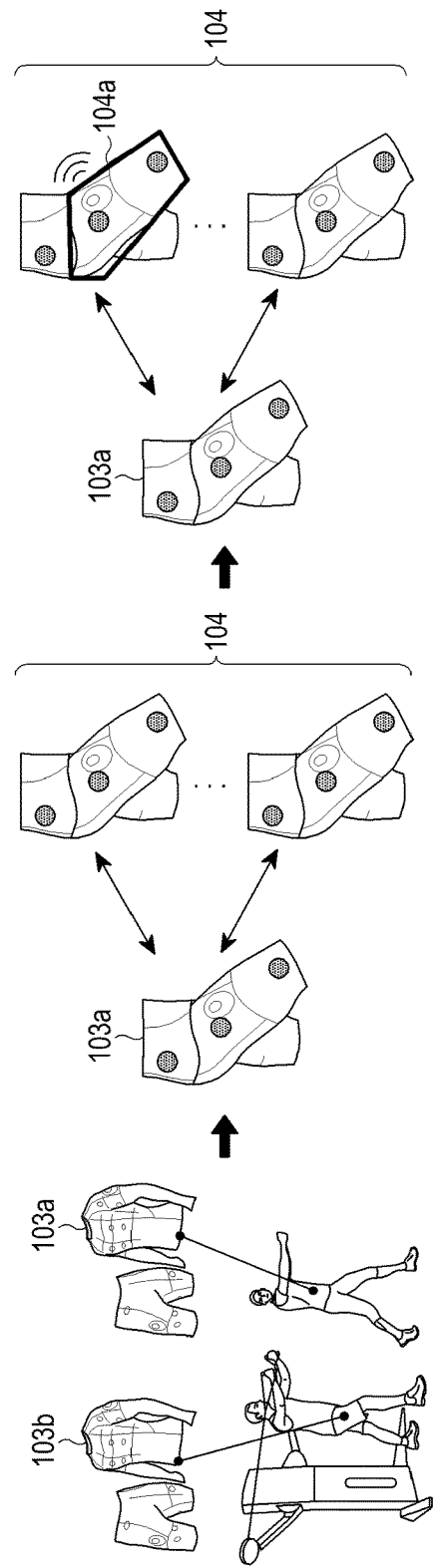

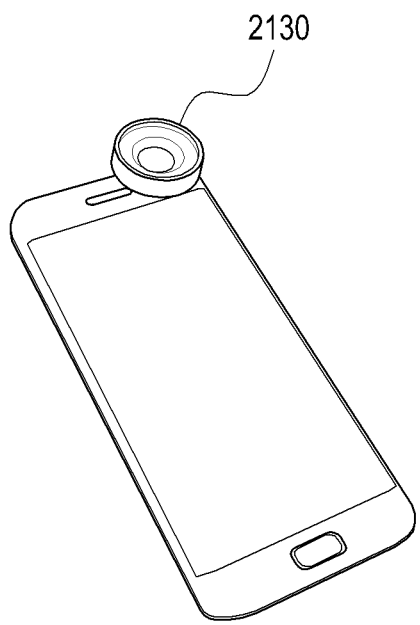
(a)
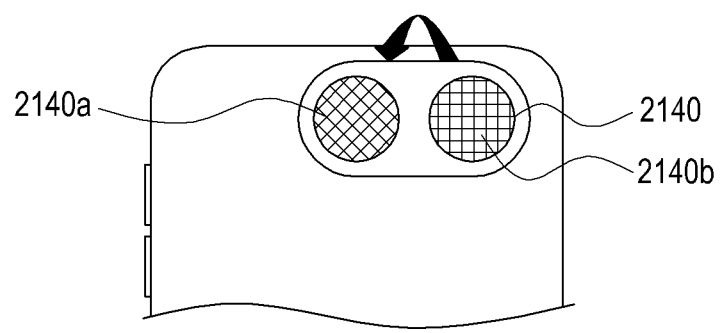
(b)
FIG.21B

WEAR SYSTEM AND METHOD FOR PROVIDING SERVICE

CROSS-REFERENCE TO RELATED APPLICATION

This application is based on and claims priority under 35 U.S.C. § 119 to a Korean patent application filed in the Korean Intellectual Property Office on Nov. 24, 2015 and assigned Serial No. 10-2015-0164937, the disclosure of which is incorporated by reference herein in its entirety.

TECHNICAL FIELD

The present disclosure relates generally to wear systems and methods for providing services.

BACKGROUND

Smart wear refers to clothing equipped with various information technology (IT) information functionalities, including clothes retaining the wearer's personal information or sports having sensors capable of measuring in real-time bio signals, such as heart rate or body temperature, and sending the information to a server in a fitness center to automatically analyze body conditions. Under development are various types of clothing including sportswear having sensors attached thereto to measure external environments such as temperature, humidity, and ultraviolet (UV) exposure or clothes for performances that change colors depending on the strength of claps or music sounds.

A user may check his body conditions using smart wear having authentication information previously registered only when putting on the smart wear. Thus, the user needs to keep wearing the smart wear having authentication information previously registered.

Since the smart wear should keep powering the components of the smart wear to sense whether the user puts on the smart wear, it may consume significant power.

The above information is presented as background information only to assist with an understanding of the present disclosure. No determination has been made, and no assertion is made, as to whether any of the above might be applicable as prior art with regard to the present disclosure.

SUMMARY

According to various example embodiments of the present disclosure, a wear system and method for providing services are provided that may recognize a user and provide relevant services to the user whatever smart wear the user puts on.

According to an example embodiment of the present disclosure, a wear system for providing a service may comprise a wear device configured to detect authentication information regarding a user wearing the wear device in a first state, to transmit the authentication information to a server, and if authentication of the user is complete through the server, to detect user data of the wear device in a second state and to transmit the user data to the server and the server is configured to complete the authentication of the user upon detecting identification information regarding the user using the authentication information received from the wear device, to generate a user profile based on the user data received from the wear device, to store the user profile corresponding to the identification information, and to provide service information related to the user to the wear device.

According to an example embodiment of the present disclosure, a method for providing a service may comprise detecting authentication information regarding a user wearing a wear device in a first state and transmitting the authentication information to a server by the wear device, completing authentication of the user by the server upon detecting the user's identification information using the authentication information received from the wear device, detecting user data of the wear device in a second state upon completing the authentication of the user through the server, and transmitting the user data to the server by the wear device, generating a user profile based on the user data received from the wear device and storing the user profile corresponding to the identification information by the server, and providing service information related to the user to the wear device by the server.

According to various example embodiments of the present disclosure, the system and method for providing services may recognize the user and provide him with relevant services anytime, anywhere, and whatever smart wear he puts on.

Other aspects, advantages, and salient features of the disclosure will become apparent to those skilled in the art from the following detailed description, which, taken in conjunction with the annexed drawings, discloses various example embodiments of the disclosure.

BRIEF DESCRIPTION OF THE DRAWINGS

A more complete appreciation of the present disclosure and many of the attendant aspects and advantages thereof will be readily obtained from the following detailed description, taken in conjunction with the accompanying drawings, in which like reference numerals refer to like elements, and wherein:

FIG. 8 is a diagram illustrating example authentication information in a server according to an example embodiment of the present disclosure

FIG. 14 is a diagram illustrating example service information provided from a server according to an example embodiment of the present disclosure;

FIGS. 18A, 18B, 18C, 19 and 20 are diagrams illustrating other examples of providing a service in a wear system for providing services according to an example embodiment of the present disclosure;

FIGS. 21A and 21B are diagrams illustrating other examples of providing a service in a wear system for providing services according to an example embodiment of the present disclosure;

Throughout the drawings, like reference numerals will be understood to refer to like parts, components, and structures.

DETAILED DESCRIPTION

Figure 1:
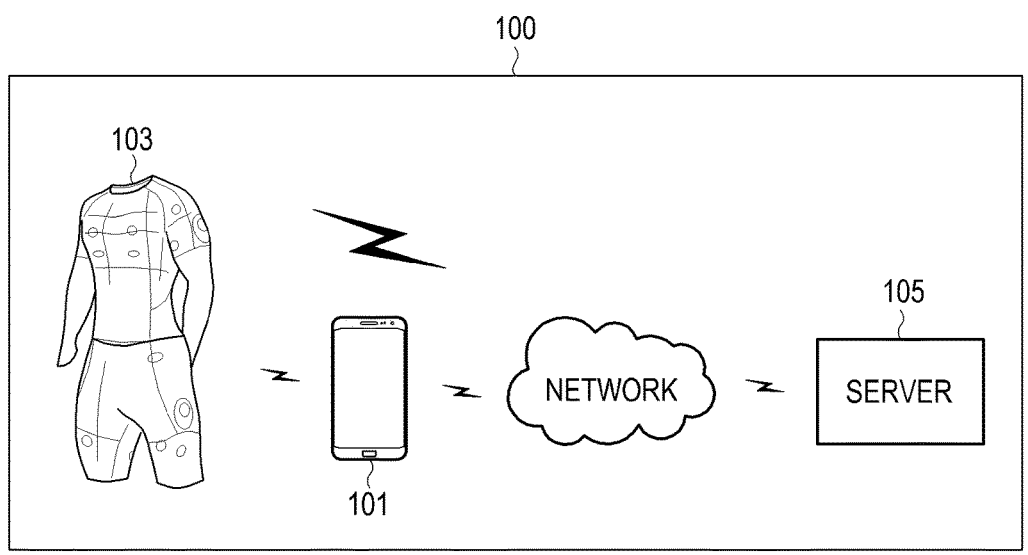
FIG. 1 is a diagram illustrating an example wear system for providing services according to an example embodiment of the present disclosure.

Hereinafter, example embodiments of the present disclosure are described with reference to the accompanying drawings. However, it should be appreciated that the present disclosure is not limited to the example embodiments, and all changes and/or equivalents or replacements thereto also fall within the scope of the present disclosure. The same or similar reference denotations may be used to refer to the same or similar elements throughout the specification and the drawings.

As used herein, the terms "have," "may have," "include," or "may include" a feature (e.g., a number, function, operation, or a component such as a part) indicate the existence of the feature and do not exclude the existence of other features.

As used herein, the terms "A or B," "at least one of A and/or B," or "one or more of A and/or B" may include all possible combinations of A and B. For example, "A or B," "at least one of A and B," "at least one of A or B" may indicate all of (1) including at least one A, (2) including at least one B, or (3) including at least one A and at least one B.

As used herein, the terms "first" and "second" may modify various components regardless of importance and/or order and are used to distinguish a component from another without limiting the components. For example, a first user device and a second user device may indicate different user devices from each other regardless of the order or importance of the devices. For example, a first component may be denoted a second component, and vice versa without departing from the scope of the present disclosure.

It will be understood that when an element (e.g., a first element) is referred to as being (operatively or communicatively) "coupled with/to," or "connected with/to" another element (e.g., a second element), it can be coupled or connected with/to the other element directly or via a third element. On the other hand, it will be understood that when an element (e.g., a first element) is referred to as being "directly coupled with/to" or "directly connected with/to" another element (e.g., a second element), no other element (e.g., a third element) intervenes between the element and the other element.

As used herein, the terms "configured (or set) to" may be used interchangeably with the terms "suitable for," "having the capacity to," "designed to," "adapted to," "made to," or "capable of" depending on circumstances. The term "configured (or set) to" does not necessarily mean "specifically designed in hardware to." Rather, the term "configured to" may refer, for example, to a situating in which a device can perform an operation together with another device or parts. For example, the term "processor configured (or set) to perform A, B, and C" may refer, for example, to processing circuitry, a generic-purpose processor (e.g., a CPU or application processor), or the like, that may perform the operations by executing one or more software programs stored in a memory device or a dedicated processor (e.g., an embedded processor including processing circuitry) for performing the operations.

The terms as used herein are provided merely to describe various example embodiments thereof, but not to limit the scope of other example embodiments of the present disclosure. It is to be understood that the singular forms "a," "an," and "the" include plural references unless the context clearly dictates otherwise. The terms including technical and scientific terms used herein have the same meaning as commonly understood by one of ordinary skill in the art to which the embodiments of the present disclosure belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

For example, examples of the electronic device according to example embodiments of the present disclosure may include at least one of a smartphone, a tablet personal computer (PC), a mobile phone, a video phone, an e-book reader, a desktop PC, a laptop computer, a netbook computer, a workstation, a personal digital assistant (PDA), a portable multimedia player (PMP), an MP3 player, a mobile medical device, a camera, or a wearable device, or the like, but is not limited thereto. According to an example embodiment of the present disclosure, the wearable device may include at least one of an accessory-type device (e.g., a watch, a ring, a bracelet, an anklet, a necklace, glasses, contact lenses, or a head-mounted device (HMD)), a fabric- or clothes-integrated device (e.g., electronic clothes), a body attaching-type device (e.g., a skin pad or tattoo), or a body implantable device (e.g., an implantable circuit), or the like, but is not limited thereto.

According to an example embodiment of the present disclosure, the electronic device may be a home appliance. Examples of the home appliance may include at least one of a television, a digital video disk (DVD) player, an audio player, a refrigerator, an air conditioner, a cleaner, an oven, a microwave oven, a washer, a drier, an air cleaner, a set-top box, a home automation control panel, a security control panel, a TV box (e.g., Samsung HomeSync™, Apple TV™, or Google TV™), a gaming console (Xbox™, PlayStation™), an electronic dictionary, an electronic key, a camcorder, or an electronic picture frame, or the like but is not limited thereto.

According to an example embodiment of the present disclosure, examples of the electronic device may include at least one of various medical devices (e.g., diverse portable medical measuring devices (a blood sugar measuring device, a heartbeat measuring device, or a body temperature measuring device), a magnetic resource angiography (MRA) device, a magnetic resource imaging (MRI) device, a computed tomography (CT) device, an imaging device, or an ultrasonic device), a navigation device, a global navigation satellite system (GNSS) receiver, an event data recorder (EDR), a flight data recorder (FDR), an automotive infotainment device, an sailing electronic device (e.g., a sailing navigation device or a gyro compass), avionics, security devices, vehicular head units, industrial or home robots, automatic teller's machines (ATMs), point of sales (POS) devices, or Internet of Things devices (e.g., a bulb, various sensors, an electric or gas meter, a sprinkler, a fire alarm, a thermostat, a street light, a toaster, fitness equipment, a hot water tank, a heater, or a boiler), or the like, but is not limited thereto.

According to various example embodiments of the disclosure, examples of the electronic device may at least one of part of a piece of furniture or building/structure, an electronic board, an electronic signature receiving device, a projector, or various measurement devices (e.g., devices for measuring water, electricity, gas, or electromagnetic waves), or the like, but is not limited thereto. According to an example embodiment of the present disclosure, the electronic device may be one or a combination of the above-listed devices. According to an example embodiment of the present disclosure, the electronic device may be a flexible electronic device. The electronic device disclosed herein is not limited to the above-listed devices, and may include new electronic devices depending on the development of technology.

Hereinafter, example wear systems and methods are described with reference to the accompanying drawings, according to various example embodiments of the present disclosure. As used herein, the term "user" may denote a human or another device (e.g., an artificial intelligent electronic device) using the electronic device.

A wear device, as used herein, may refer, for example, to a smart wear article, e.g., an article of clothing including various clothing equipped with various information technology (IT) functionalities, including, for example, and without limitation, a clothing article provided with sensors, various communication technology and/or processing technology. An article of clothing of the wear device may include, for example, and without limitation, a shirt, shorts, pants, socks, shoes, undergarments, or any other article configured to be worn on the torso of a user. As used herein, clothing is not limited to any particular material or type of cloth and may include various constructions in addition to those enumerated above, such as, for example, and without limitation, a strap, a sleeve, a brace, or the like configured to be worn on the torso of a user.

FIG. 1 is a block diagram illustrating an example wear system for providing services according to an example embodiment of the present disclosure. Referring to FIG. 1, the wear system 100 may include an electronic device 101, a smart wear device 103, and a server 105.

According to an example embodiment of the present disclosure, the electronic device 101 may transmit authentication information or user data, received from the smart wear device 103, to the server 105 while in communication connection with the smart wear device 103. The electronic device 101 may transmit service information related to the user wearing the smart wear device 103, which is received from the server 105, to the smart wear device 103. The electronic device 101 may establish a communication connection with the smart wear device 103 through a short-range communication unit. A configuration of the electronic device 101 is described below in greater detail with reference to FIG. 2.

According to an example embodiment of the present disclosure, the smart wear device 103 may detect authentication information regarding the user wearing the smart wear device 103 in a low-power, first state, transmit the detected authentication information to the server 105 directly or through the electronic device 101, detect user data indicating an operational state of the smart wear device 103 in a second state different from the first state, and transmit the detected user data to the server 105 directly or through the electronic device 101. The smart wear device 103 may receive service information related to the user wearing the smart wear device 103 from the server 105 directly or through the electronic device 101. A configuration of the smart wear device 103 is described in greater detail below with reference to FIG. 3.

According to an example embodiment of the present disclosure, the server 105 may store a user profile and authentication information corresponding to each of a plurality of identification information, detect the identification information regarding the user wearing the smart wear device 103 using the authentication information received from the smart wear device 103, and transmit service information detected based on the user profile corresponding to the identification information to the smart wear device 103 directly or through the electronic device 101. A configuration of the server 103 is described in greater detail below with reference to FIG. 5.

Figure 2:
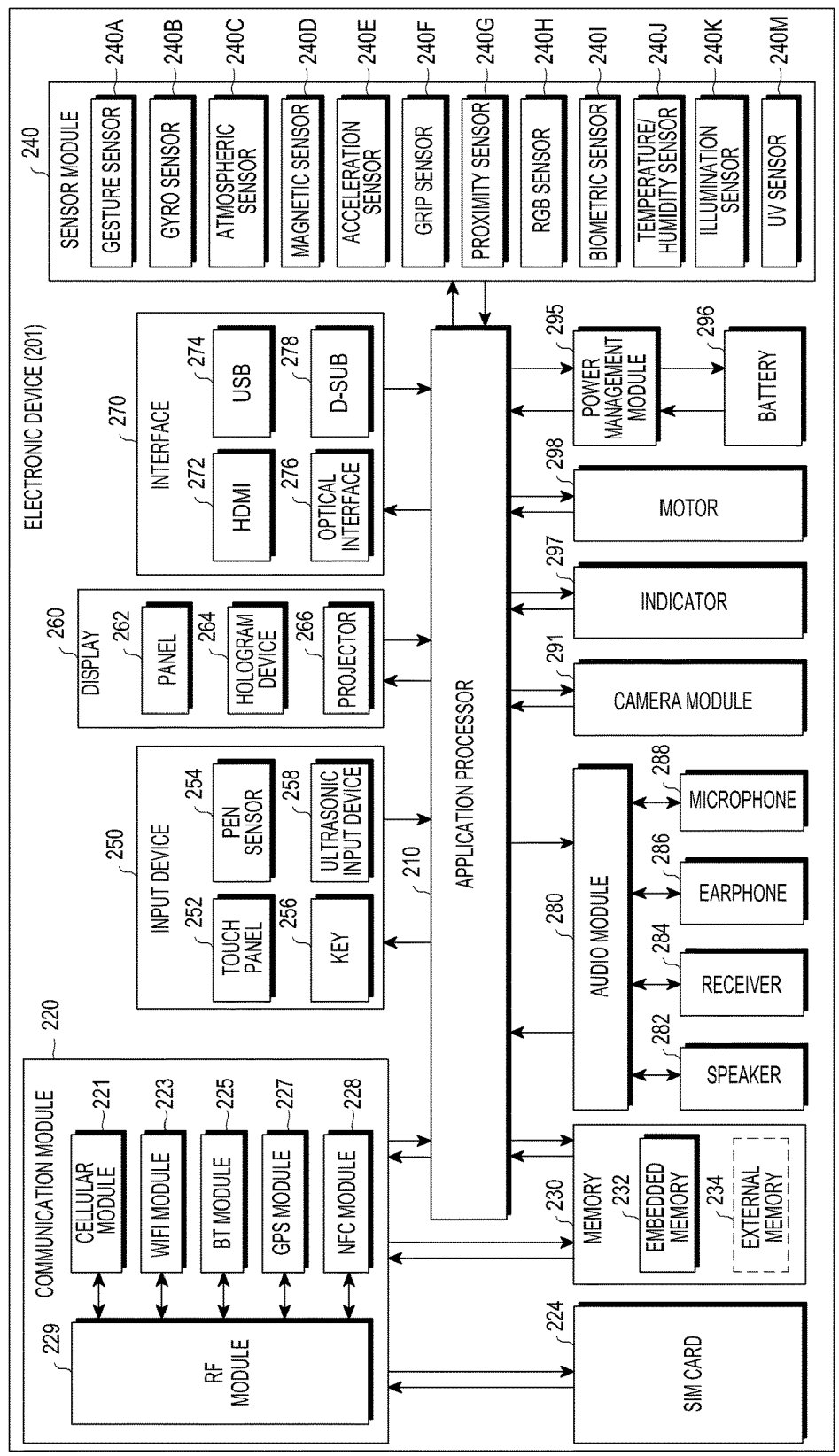
FIG. 2 is a block diagram illustrating an example electronic device according to an example embodiment of the present disclosure.

FIG. 2 is a block diagram illustrating an example electronic device 201 according to an example embodiment of the present disclosure. The electronic device 201 may include the whole or part of the configuration of, e.g., the electronic device 101 illustrated in FIG. 1. The electronic device 201 may include one or more processors (e.g., application processors (APs)) (e.g., including processing circuitry) 210, a communication module (e.g., including communication circuitry) 220, a subscriber identification module (SIM) 224, a memory 230, a sensor module 240, an input device (e.g., including input circuitry) 250, a display 260, an interface (e.g., including interface circuitry) 270, an audio module 280, a camera module 291, a power management module 295, a battery 296, an indicator 297, and a motor 298.

The processor 210 may include various processing circuitry configured to control multiple hardware and software components connected to the processor 210 by running, e.g., an operating system or application programs, and the processor 210 may process and compute various data. The processor 210 may be implemented using various processing circuitry, including, e.g., a system on chip (SoC). According to an example embodiment of the present disclosure, the processor 210 may further include a graphic processing unit (GPU) and/or an image signal processor. The processor 210 may include at least some (e.g., the cellular module 221) of the components shown in FIG. 2. The processor 210 may load a command or data received from at least one of other components (e.g., a non-volatile memory) on a volatile memory, process the command or data, and store various data in the non-volatile memory.

According to an example embodiment of the present disclosure, the processor 210 may transmit authentication information and user data to the server (the server 105 of FIG. 1), which is received from the wear device (the smart wear device 103 of FIG. 1), while in communication connection with the wear device.

According to an example embodiment of the present disclosure, the processor 210 may perform Bluetooth communication with the wear device using a short-range communication module, e.g., the Bluetooth module 225.

According to an example embodiment of the present disclosure, the processor 210 may store user data received from the wear device.

According to an example embodiment of the present disclosure, the processor 210 may transmit service information related to the user wearing the wear device which is received from the server to the wear device.

According to an example embodiment of the present disclosure, the processor 210 may access the server in the user's authentication information registration mode to register new identification information (e.g., global unique identification (GUID)) and may access the server and remain logged in so that authentication information regarding the wear device may be registered in the server.

The communication module 220 may include various communication circuitry, such as, for example, and without limitation, a cellular module 221, a wireless fidelity (Wi-Fi) module 223, a Bluetooth (BT) module 225, a GNSS module 227, a NFC module 228, and a RF module 229.

The cellular module 221 may provide voice call, video call, text, or Internet services through, e.g., a communication network. The cellular module 221 may perform identification or authentication on the electronic device 201 in the communication network using a subscriber identification module 224 (e.g., the SIM card). According to an example embodiment of the present disclosure, the cellular module 221 may perform at least some of the functions providable by the processor 210. According to an example embodiment of the present disclosure, the cellular module 221 may include a communication processor (CP).

The Wi-Fi module 223, the Bluetooth module 225, the GNSS module 227, or the NFC module 228 may include a process for, e.g., processing data communicated through the module. According to an embodiment of the present disclosure, at least some (e.g., two or more) of the cellular module 221, the Wi-Fi module 223, the Bluetooth module 225, the GNSS module 227, or the NFC module 228 may be included in a single integrated circuit (IC) or an IC package.

The RF module 229 may communicate data, e.g., communication signals (e.g., RF signals). The RF module 229 may include, e.g., a transceiver, a power amplifier module (PAM), a frequency filter, a low noise amplifier (LNA), or an antenna. According to an embodiment of the present disclosure, at least one of the cellular module 221, the Wi-Fi module 223, the Bluetooth module 225, the GNSS module 227, or the NFC module 228 may communicate RF signals through a separate RF module.

The subscription identification module 224 may include, e.g., a card including a subscriber identification module and/or an embedded SIM, and may contain unique identification information (e.g., an integrated circuit card identifier (ICCID) or subscriber information (e.g., an international mobile subscriber identity (IMSI)).

The memory 230 (e.g., the memory 130) may include, e.g., an internal memory 232 and/or an external memory 234. The internal memory 232 may include at least one of, e.g., a volatile memory (e.g., a dynamic RAM (DRAM), a static RAM (SRAM), a synchronous dynamic RAM (SDRAM), etc.) or a non-volatile memory (e.g., a one-time programmable ROM (OTPROM), a programmable ROM (PROM), an erasable and programmable ROM (EPROM), an electrically erasable and programmable ROM (EEPROM), a mask ROM, a flash ROM, a flash memory (e.g., a NAND flash, or a NOR flash), a hard drive, or solid state drive (SSD).

The external memory 234 may include a flash drive, e.g., a compact flash (CF) memory, a secure digital (SD) memory, a micro-SD memory, a min-SD memory, an extreme digital (xD) memory, a multi-media card (MMC), or a memory stick™. The external memory 234 may be functionally and/or physically connected with the electronic device 201 via various interfaces.

For example, the sensor module 240 may measure a physical quantity or detect a motion state of the electronic device 201, and the sensor module 240 may convert the measured or detected information into an electrical signal. The sensor module 240 may include at least one of, e.g., a gesture sensor 240A, a gyro sensor 240B, an atmospheric pressure sensor 240C, a magnetic sensor 240D, an acceleration sensor 240E, a grip sensor 240F, a proximity sensor 240G, a color sensor 240H (e.g., a red-green-blue (RGB) sensor, a biometric sensor 240I, a temperature/humidity sensor 240J, an illumination sensor 240K, or an Ultra Violet (UV) sensor 240M. Additionally or alternatively, the sensing module 240 may include, e.g., an e-nose sensor, an electromyography (EMG) sensor, an electroencephalogram (EEG) sensor, an electrocardiogram (ECG) sensor, an infrared (IR) sensor, an iris sensor, or a finger print sensor. The sensor module 240 may further include a control circuit for controlling at least one or more of the sensors included in the sensing module. According to an example embodiment of the present disclosure, the electronic device 201 may further include a processor configured to control the sensor module 240 as part of the processor 210 or separately from the processor 210, and the electronic device 2701 may control the sensor module 240 while the processor 210 is in a sleep mode.

The input unit 250 may include various input circuitry, such as, for example, and without limitation, a touch panel 252, a (digital) pen sensor 254, a key 256, or an ultrasonic input device 258. The touch panel 252 may use at least one of capacitive, resistive, infrared, or ultrasonic methods. The touch panel 252 may further include a control circuit. The touch panel 252 may further include a tactile layer and may provide a user with a tactile reaction.

The (digital) pen sensor 254 may include, e.g., a part of a touch panel or a separate sheet for recognition. The key 256 may include e.g., a physical button, optical key or key pad. The ultrasonic input device 258 may sense an ultrasonic wave generated from an input tool through a microphone (e.g., the microphone 288) to identify data corresponding to the sensed ultrasonic wave.

The display 260 (e.g., the display 160) may include a panel 262, a hologram device 264, or a projector 266. The panel 262 may be implemented to be flexible, transparent, or wearable. The panel 262 may also be incorporated with the touch panel 252 in a module. The hologram device 264 may make three dimensional (3D) images (holograms) in the air by using light interference. The projector 266 may display an image by projecting light onto a screen. The screen may be, for example, located inside or outside of the electronic device 201. In accordance with an embodiment, the display 260 may further include a control circuit to control the panel 262, the hologram device 264, or the projector 266.

The interface 270 may include various interface circuitry, such as, for example, and without limitation, a high definition multimedia interface (HDMI) 272, a USB 274, an optical interface 276, or a D-subminiature (D-sub) 278. The interface 270 may be included in e.g., the communication interface 170 shown in FIG. 1. Additionally or alternatively, the interface 270 may include a mobile high-definition link (MHL) interface, a secure digital (SD) card/multimedia card (MMC) interface, or infrared data association (IrDA) standard interface.

The audio module 280 may convert a sound into an electric signal or vice versa, for example. The audio module 280 may process sound information input or output through e.g., a speaker 282, a receiver 284, an earphone 286, or a microphone 288.

For example, the camera module 291 may be a device for recording still images and videos, and may include, according to an example embodiment of the present disclosure, one or more image sensors (e.g., front and back sensors), a lens, an Image signal processor (ISP), or a flash such as an LED or xenon lamp.

The power manager module 295 may manage power of the electronic device 201, for example. According to an embodiment of the present disclosure, the power manager module 295 may include a power management Integrated circuit (PMIC), a charger IC, or a battery or fuel gauge. The PMIC may have a wired and/or wireless recharging scheme. The wireless charging scheme may include e.g., a magnetic resonance scheme, a magnetic induction scheme, or an electromagnetic wave based scheme, and an additional circuit, such as a coil loop, a resonance circuit, a rectifier, or the like may be added for wireless charging. The battery gauge may measure an amount of remaining power of the battery 296, a voltage, a current, or a temperature while the battery 296 is being charged. The battery 296 may include, e.g., a rechargeable battery or a solar battery.

The indicator 297 may indicate a particular state of the electronic device 201 or a part (e.g., the processor 210) of the electronic device, including e.g., a booting state, a message state, or recharging state. The motor 298 may convert an electric signal to a mechanical vibration and may generate a vibrational or haptic effect. Although not shown, a processing unit for supporting mobile TV, such as a GPU may be included in the electronic device 201. The processing unit for supporting mobile TV may process media data conforming to a standard for digital multimedia broadcasting (DMB), digital video broadcasting (DVB), or mediaFlo™.

Each of the aforementioned components of the electronic device may include one or more parts, and a name of the part may vary with a type of the electronic device. The electronic device in accordance with various example embodiments of the present disclosure may include at least one of the aforementioned components, omit some of them, or include other additional component(s). Some of the components may be combined into an entity, but the entity may perform the same functions as the components may do.

Figure 3:
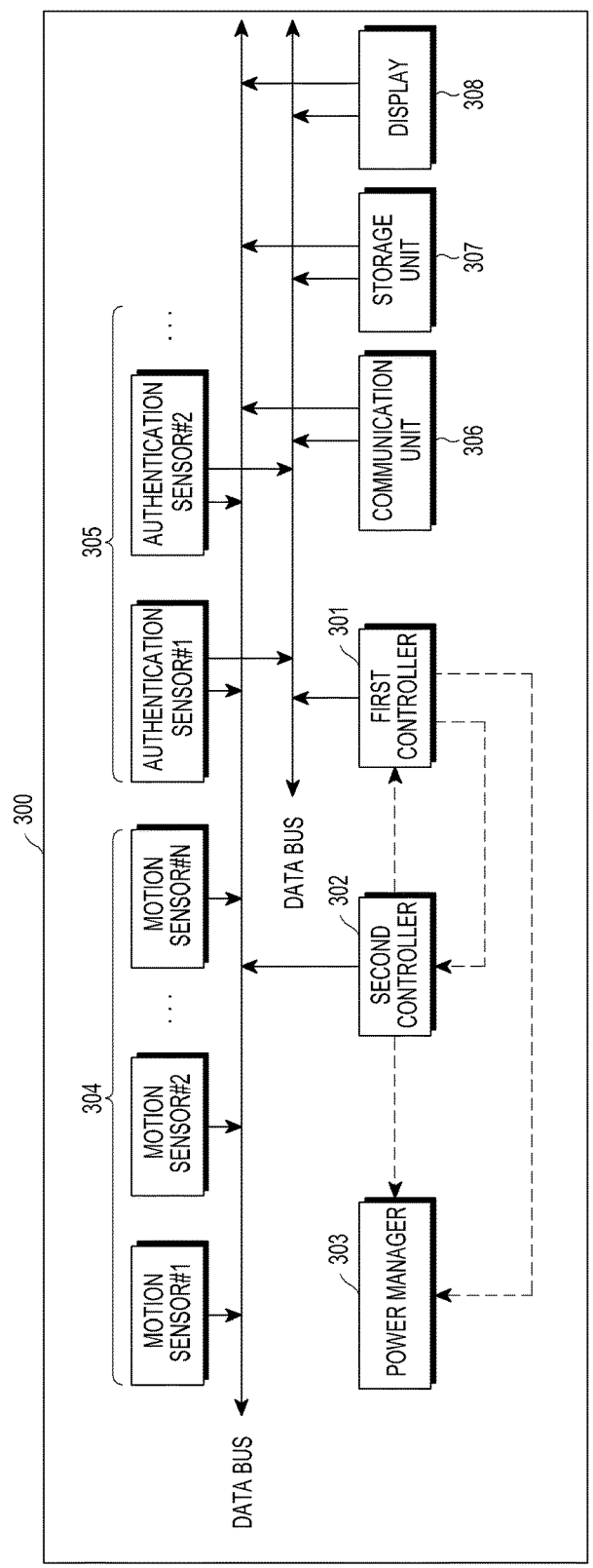
FIG. 3 is a block diagram illustrating an example wear device according to an example embodiment of the present disclosure.

FIG. 3 is a block diagram illustrating an example wear device 300 according to an example embodiment of the present disclosure. The smart wear device 300 may include all or some of the components of, e.g., the wear device 103 of FIG. 1. The wear device 300 may include a first controller (e.g., including processing circuitry) 301, a second controller (e.g., including processing circuitry) 302, a power manager 303, a plurality of sensors 304 and 305, a communication unit (e.g. including communication circuitry) 306, a storage unit 307 and a display 308.

According to an example embodiment of the present disclosure, the first controller 301 may detect authentication information regarding the user wearing the wear device 300 in a first state, transmit the detected authentication information to the server (the server 105 of FIG. 1), and when the user is completely authenticated, switch into a second state where the second controller 302 wakes up.

According to an example embodiment of the present disclosure, the first controller 301 may detect whether sensor signals are output from the authentication sensors 305 while repeating wakeup and sleep at predetermined periods. The first controller 301 may detect whether the user wears the wear device 300 using sensor signals output from the authentication sensors 305 and may detect the sensor signals as authentication information regarding the user wearing the wear device 300 and transmit the sensor signals to the server. The sensor signals may be, e.g., bio signals.

According to an example embodiment of the present disclosure, the first controller 301 may include a low-power micro controller unit (MCU).

According to an example embodiment of the present disclosure, the first controller 301 may control (e.g., power on/off) the powering of the authentication sensors 305 through the power manager 303.

According to an example embodiment of the present disclosure, when receiving authentication complete information regarding the user wearing the wear device 300 from the server, the first controller 301 may wake up the second controller 302 and switch into a second state where the first controller 301 is put into a sleep state.

According to an example embodiment of the present disclosure, the first state may refer, for example, to a state in which, in a low-power, standby state, the first controller 301 periodically wakes up, and the second controller 302 remains in the sleep state, and the second state may refer, for example, to a state in which, in a normal power consuming state, the second controller 302 wakes up, and the first controller 301 remains in the sleep state. The first state and the second state are described in greater detail below with reference to FIG. 4.

Figure 4:
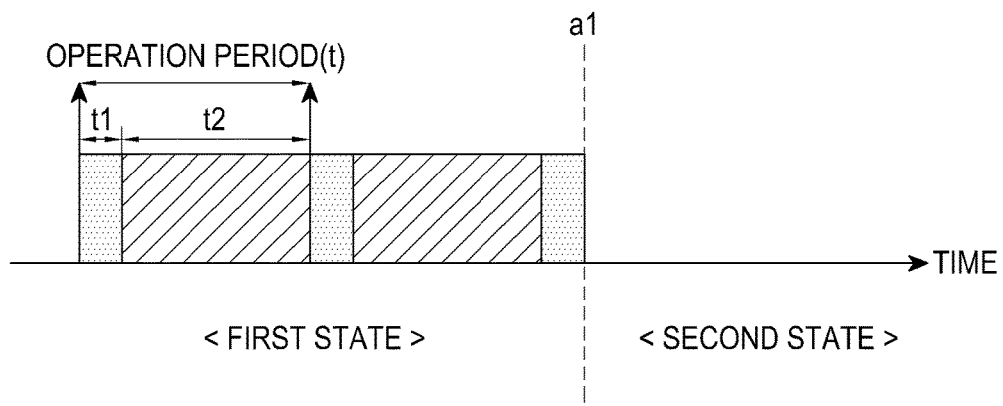
FIG. 4 is a diagram illustrating example operations of a low-power controller in a wear device according to an example embodiment of the present disclosure.

FIG. 4 is a diagram illustrating example operations of a low-power controller in a wear device according to an example embodiment of the present disclosure.

Referring to FIG. 4, in the first state which is a low-power, standby state, the first controller 301 may repeat a wakeup state t1 and a sleep state t2 during a predetermined operation period t and identify sensor signals output from the authentication sensors 305. In the first state, the second controller remains in the sleep state. At a time a1 when authentication is complete for the user wearing the wear device while the first state remains, the wear device switches into the second state, and in the second state, the second controller 302 wakes up, and the first controller remains in the sleep state.

According to an example embodiment of the present disclosure, the second controller 302 may detect user data of the wear device 300 using motion sensors 304 and authentication sensors 305 in the second state and transmit the detected user data to the server.

According to an example embodiment of the present disclosure, the second controller 302 may detect sensor signals received from the motion sensors 304 and authentication sensors 305 in the second state, detect sensor information including sensor types, sensor signal values, or a context (e.g., position of sensor and time that sensor signal is detected), as user data indicating the operational state of the wear device, and transmit the sensor information to the server 105.

According to an example embodiment of the present disclosure, the second controller 302 may control (e.g., power on/off) the powering of the motion sensors 304 and authentication sensors 305 through the power manager 303.

According to an example embodiment of the present disclosure, while new identification information (e.g., global unique identification (GUID)) is generated and registered in the server through an electronic device (e.g., the electronic device 101 of FIG. 1) in a mode of registering the user's authentication information, the second controller 302 may transmit sensor signals received from the authentication sensors 305 to the server to register authentication information corresponding to the identification information.

According to an example embodiment of the present disclosure, the second controller 302 may transmit configuration information of the wear device to the server and receive service information corresponding to the configuration information of the wear device 300. The configuration information of the wear device may include, for example, specification information (e.g., capacity of storage unit or whether a display is present) regarding hardware included in the wear device and sensor information.

According to an example embodiment of the present disclosure, upon failing to receive sensor signals from the authentication sensors 305, the second controller 302 may detect the user taking off the wear device, wake up the first controller, and switch into the first state where the second controller 302 turns into the sleep state.

According to an example embodiment of the present disclosure, when communication with the server is impossible, the second controller 302 may store user data in the storage unit of the wear device or an electronic device connected through communication with the wear device. Thereafter, when the wear device establishes a communication connection with the server, the user data stored in the wear device or electronic device may be transmitted to the server to be synced.

According to an example embodiment of the present disclosure, the second controller 302 may send a request for a user profile stored corresponding to the identification information regarding the user of the wear device and receive the user profile through direct communication with the server or via the electronic device.

According to an example embodiment of the present disclosure, when communication with the server is impossible, the second controller 302 may load a snap shot of the user profile or user data stored in the electronic device connected via communication with the wear device or the storage unit of the wear device.

According to an example embodiment of the present disclosure, the plurality of sensors may include authentication sensors 305 for detecting authentication information of the user wearing the wear device and motion sensors 306 for detecting motions of the user wearing the wear device.

The authentication sensors 305 may, for example, be sensors capable of detecting bio signals and may include, for example, and without limitation, an ECG sensor, an EMG sensor, and a heartbeat sensor. The motion sensors 304 may, for example, be sensors capable of detecting motions of the user wearing the wear device and may include, for example, and without limitation, an acceleration sensor, a gyro sensor, and a location sensor.

According to an example embodiment of the present disclosure, the communication unit 306 may include various communication circuitry configured to transmit user data indicating an operational state to the server or the electronic device.

According to an example embodiment of the present disclosure, when the communication unit 306 includes a RF unit for communication with the server, the communication unit 306 may transmit the user data to the server upon establishing a communication connection with the server.

According to an example embodiment of the present disclosure, when the communication unit 306 does not include a RF unit for communication with the server and include a short range communication module for the electronic device, the communication unit 306 may transmit the user data to the server through the electronic device upon establishing a communication connection with the electronic device.

According to an example embodiment of the present disclosure, the storage unit 307 may store the user data indicating the operational state of the wear device.

According to an example embodiment of the present disclosure, the display 308 may display contents received or stored in the wear device 300.

Figure 5:
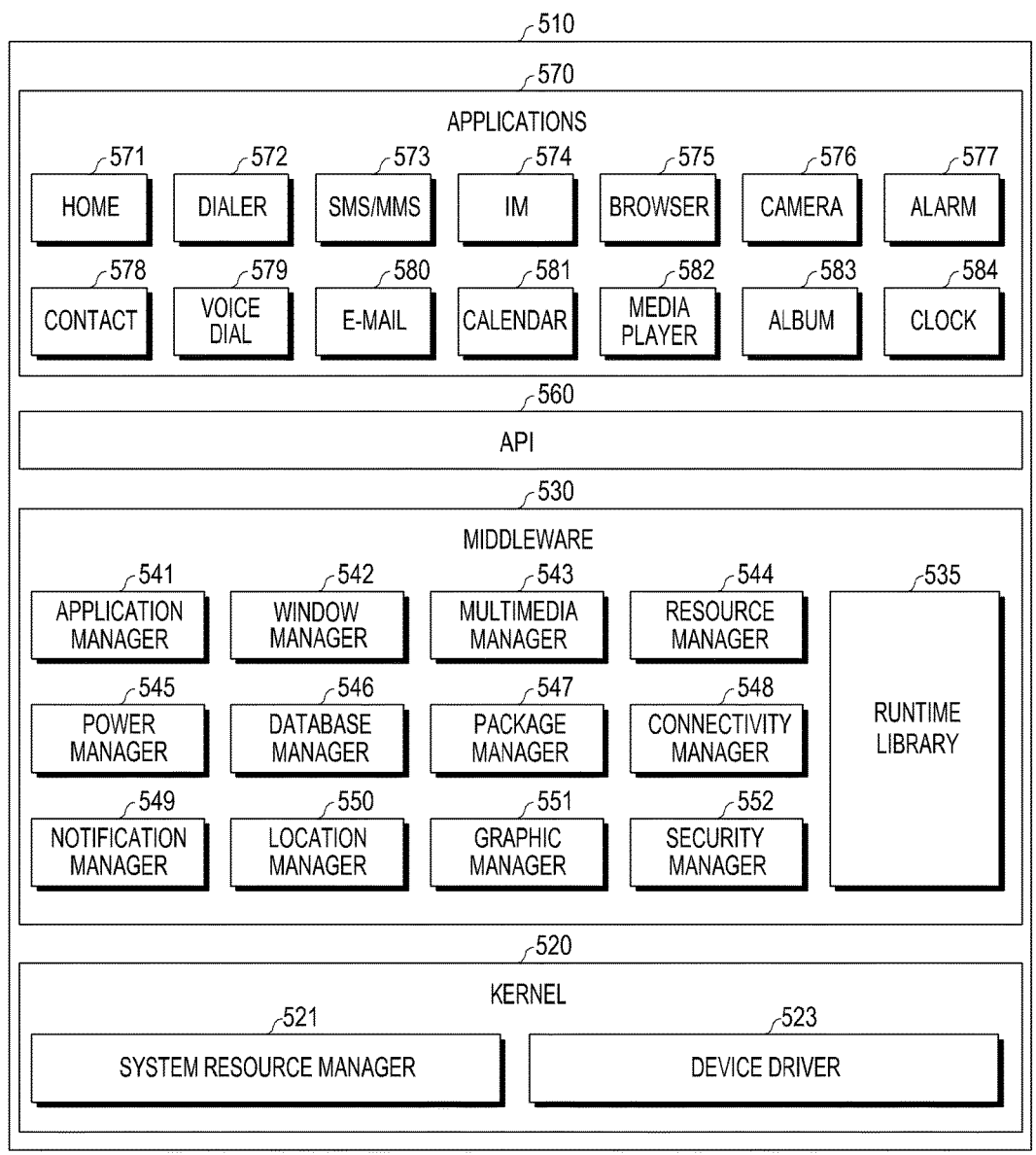
FIG. 5 is a block diagram illustrating an example program module according to an example embodiment of the present disclosure.

FIG. 5 is a block diagram illustrating an example program module according to an example embodiment of the present disclosure. According to an example embodiment of the present disclosure, the program module 510 (e.g., the program 140) may include an operating system (OS) controlling resources related to the electronic device (e.g., the electronic device 101 of FIG. 1) or wear device (e.g., the wear device 103 of FIG. 1) and/or various applications (e.g., the application processor 147) driven on the operating system. The operating system may include, e.g., Android, iOS, Windows, Symbian, Tizen, or Bada.

The program 510 may include, e.g., a kernel 520, middleware 530, an application programming interface (API) 560, and/or an application 570. At least a part of the program module 510 may be preloaded on the electronic device or may be downloaded from an external electronic device (e.g., the electronic devices 102 and 104 or server 106).

The kernel 520 (e.g., the kernel 141) may include, e.g., a system resource manager 521 and/or a device driver 523. The system resource manager 521 may perform control, allocation, or recovery of system resources. According to an example embodiment of the present disclosure, the system resource manager 521 may include a process managing unit, a memory managing unit, or a file system managing unit. The device driver 523 may include, e.g., a display driver, a camera driver, a Bluetooth driver, a shared memory driver, a USB driver, a keypad driver, a Wi-Fi driver, an audio driver, or an inter-process communication (IPC) driver.

The middleware 530 may provide various functions to the application 570 through the API 560 so that the application 570 may efficiently use limited system resources in the electronic device or provide functions jointly required by applications 570. According to an example embodiment of the present disclosure, the middleware 530 (e.g., the middleware 143) may include at least one of a runtime library 535, an application manager 541, a window manager 542, a multimedia manager 543, a resource manager 544, a power manager 545, a database manager 546, a package manager 547, a connectivity manager 548, a notification manager 549, a location manager 550, a graphic manager 551, or a security manager 552.

The runtime library 535 may include a library module used by a compiler in order to add a new function through a programming language while, e.g., the application 570 is being executed. The runtime library 535 may perform input/output management, memory management, or operation on arithmetic functions.

The application manager 541 may manage the life cycle of at least one application of, e.g., the applications 570. The window manager 542 may manage GUI resources used on the screen. The multimedia manager 543 may grasp formats necessary to play various media files and use a codec appropriate for a format to perform encoding or decoding on media files. The resource manager 544 may manage resources, such as source code of at least one of the applications 570, memory or storage space.

The power manager 545 may operate together with, e.g., a basic input/output system (BIOS) to manage battery or power and provide power information necessary for operating the electronic device. The database manager 546 may generate, search, or vary a database to be used in at least one of the applications 570. The package manager 547 may manage installation or update of an application that is distributed in the form of a package file.

The connectivity manager 548 may manage wireless connectivity, such as, e.g., Wi-Fi or Bluetooth. The notification manager 549 may display or notify an event, such as a coming message, appointment, or proximity notification, of the user without interfering with the user. The location manager 550 may manage locational information on the electronic device. The graphic manager 551 may manage graphic effects to be offered to the user and their related user interface. The security manager 552 may provide various security functions necessary for system security or user authentication. According to an example embodiment of the present disclosure, when the electronic device (e.g., the electronic device 101) has telephony capability, the middleware 530 may further include a telephony manager for managing voice call or video call functions of the electronic device.

The middleware 530 may include a middleware module forming a combination of various functions of the above-described components. The middleware 530 may provide a specified module per type of the operating system in order to provide a differentiated function. Further, the middleware 530 may dynamically omit some existing components or add new components.

The API 560 (e.g., the API 145) may be a set of, e.g., API programming functions and may have different configurations depending on operating systems. For example, in the case of Android or iOS, one API set may be provided per platform, and in the case of Tizen, two or more API sets may be offered per platform.

The application 570 (e.g., the application processor 147) may include one or more applications that may provide functions such as, e.g., a home 571, a dialer 572, a short message service (SMS)/multimedia messaging service (MMS) 573, an instant message (IM) 574, a browser 575, a camera 576, an alarm 577, a contact 578, a voice dial 579, an email 580, a calendar 581, a media player 582, an album 583, or a clock 584, a health-care (e.g., measuring the degree of workout or blood sugar), or provision of environmental information (e.g., provision of air pressure, moisture, or temperature information).

According to an example embodiment of the present disclosure, the application 570 may include an application (hereinafter, "information exchanging application" for convenience) supporting information exchange between the electronic device (e.g., the electronic device 101) and an external electronic device (e.g., the electronic devices 102 and 104). Examples of the information exchange application may include, but is not limited to, a notification relay application for transferring specific information to the external electronic device, or a device management application for managing the external electronic device.

For example, the notification relay application may include a function for relaying notification information generated from other applications of the electronic device (e.g., the SMS/MMS application, email application, health-care application, or environmental information application) to the external electronic device (e.g., the electronic devices 102 and 104). Further, the notification relay application may receive notification information from, e.g., the external electronic device and may provide the received notification information to the user.

The device management application may perform at least some functions of the external electronic device (e.g., the electronic device 102 or 104) communicating with the electronic device (for example, turning on/off the external electronic device (or some components of the external electronic device) or control of brightness (or resolution) of the display), and the device management application may manage (e.g., install, delete, or update) an application operating in the external electronic device or a service (e.g., call service or message service) provided from the external electronic device.

According to an example embodiment of the present disclosure, the application 370 may include an application (e.g., a health-care application of a mobile medical device) designated according to an attribute of the external electronic device (e.g., the electronic devices 102 and 104). According to an embodiment of the present disclosure, the application 570 may include an application received from the external electronic device (e.g., the server 106 or electronic devices 102 and 104). According to an example embodiment of the present disclosure, the application 570 may include a preloaded application or a third party application downloadable from a server. The names of the components of the program module 510 according to the shown embodiment may be varied depending on the type of operating system.

According to an example embodiment of the present disclosure, at least a part of the program module 510 may be implemented in software, firmware, hardware (e.g., circuitry), or in a combination of two or more thereof. At least a part of the programming module 510 may be implemented (e.g., executed) by e.g., a processor (e.g., the processor 210). At least a part of the program module 510 may include e.g., a module, program, routine, set of instructions, process, or the like for performing one or more functions.

The term 'module' may refer to a unit including one of hardware (e.g., circuitry), software, and firmware, or a combination thereof. The term 'module' may be interchangeably used with a unit, logic, logical block, component, or circuit. The module may be a minimum unit or part of an integrated component. The module may be a minimum unit or part of performing one or more functions. The module may be implemented mechanically or electronically. For example, the module may include at least one of processing circuitry, Application Specific Integrated Circuit (ASIC) chips, Field Programmable Gate Arrays (FPGAs), or Programmable Logic Arrays (PLAs) that perform some operations, which have already been known or will be developed in the future.

According to an example embodiment of the present disclosure, at least a part of the device (e.g., modules or their functions) or method (e.g., operations) may be implemented as instructions stored in a computer-readable storage medium e.g., in the form of a program module. The instructions, when executed by a processor (e.g., the processor 120), may enable the processor to carry out a corresponding function. The computer-readable storage medium may be e.g., the memory 130.

The computer-readable storage medium may include a hardware device, such as hard discs, floppy discs, and magnetic tapes (e.g., a magnetic tape), optical media such as compact disc ROMs (CD-ROMs) and digital versatile discs (DVDs), magneto-optical media such as floptical disks, ROMs, RAMs, flash memories, and/or the like. Examples of the program instructions may include not only machine language codes but also high-level language codes which are executable by various computing means using an interpreter. The aforementioned hardware devices may be configured to operate as one or more software modules to carry out example embodiments of the present disclosure, and vice versa.

Modules or programming modules in accordance with various example embodiments of the present disclosure may include at least one or more of the aforementioned components, omit some of them, or further include other additional components. Operations performed by modules, programming modules or other components in accordance with various example embodiments of the present disclosure may be carried out sequentially, simultaneously, repeatedly, or heuristically. Furthermore, some of the operations may be performed in a different order, or omitted, or include other additional operation(s). The example embodiments disclosed herein are proposed for description and understanding of the disclosed technology and does not limit the scope of the present disclosure. Accordingly, the scope of the present disclosure should be understood as including all changes or various example embodiments based on the technical spirit of the present disclosure.

Figure 6:
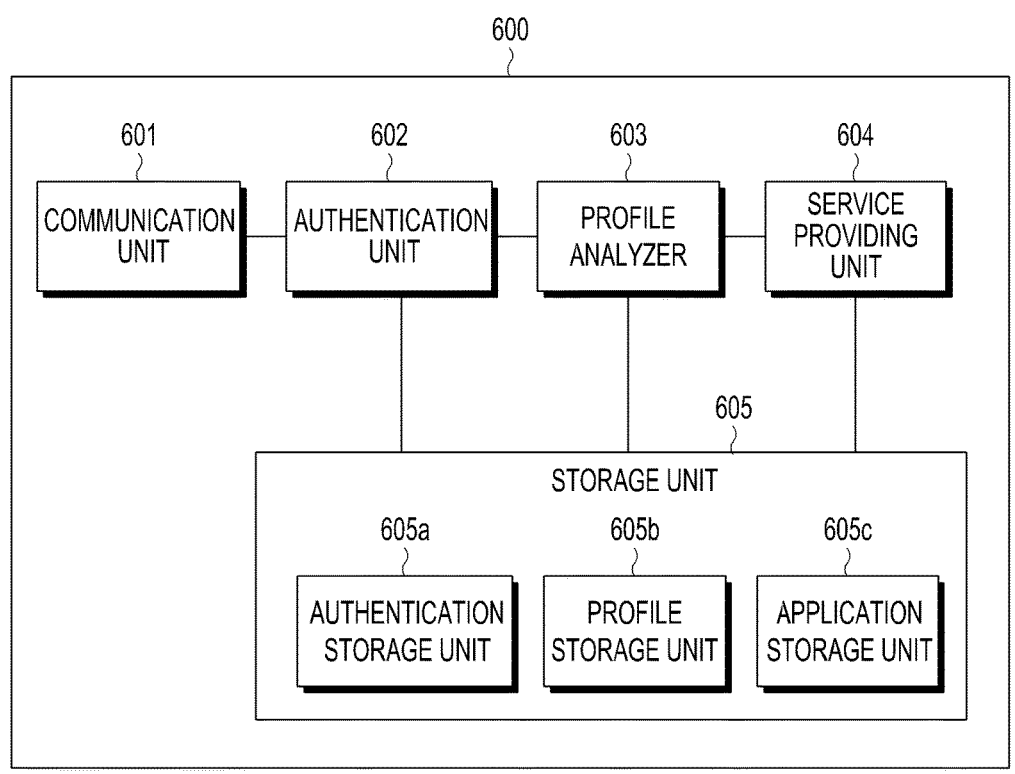
FIG. 6 is a block diagram illustrating an example server according to an example embodiment of the present disclosure.

FIG. 6 is a block diagram illustrating an example server 600 according to an example embodiment of the present disclosure. The server 600 may include the whole or part of the server 105 illustrated in FIG. 1, for example. The server 600 may include a communication unit (e.g., including communication circuitry) 601, an authentication unit 602, a profile analyzer 603, a service providing unit 604, and a storage unit 605.

According to an example embodiment of the present disclosure, the communication unit 601 may include various communication circuitry for establishing a communication connection with a wear device (e.g., the wear device 103 of FIG. 1) or an electronic device connected via communication with the wear device, may receive authentication information regarding a user wearing the wear device from the wear device and transmit service information related to the user wearing the wear device to the wear device.

According to an example embodiment of the present disclosure, the authentication unit 602 may detect identification information regarding the user wearing the wear device using the authentication information received from the wear device. The authentication unit may be realized, for example, and without limitation by processing circuitry, such as, for example, and without limitation, a processor, dedicated processor, application-specific integrated circuit, field-programmable gate array (FPGA), logic circuitry, application processor, or the like, executing program instructions.

According to an example embodiment of the present disclosure, upon receiving the authentication information from the wear device, if authentication information matching the authentication information received from the wear device is among a plurality of authentication information respectively corresponding to a plurality of identification information stored in an authentication information storage unit 605*a* of the storage unit 605, the authentication unit 602 may detect identification information corresponding to the matching authentication information and transmit authentication success information to the wear device through the communication unit 601.

According to an example embodiment of the present disclosure, the authentication unit 602 may store, in new identification information (e.g., a GUID) generated through the electronic device in a user authentication information registration mode, the authentication information received from the wear device as authentication information corresponding to the identification information.

According to an example embodiment of the present disclosure, in the user authentication information registration mode where the electronic device generates new identification information and accesses and logs in the server, the authentication unit 602, upon receiving first authentication information (e.g., an ECG sensor signal) from a first wear device, may store the first authentication information as new authentication information corresponding to the identification information. Further, upon reception of second authentication information (e.g., a heart rate signal) different from the first authentication information (e.g., the ECG sensor signal) from a second wear device, the authentication unit 602 may store the second authentication information as additional authentication information corresponding to the identification information. When receiving the first authentication information (e.g., the ECG sensor signal) from a third wear device, the authentication unit 602 may use the existing first authentication corresponding to the identification information.

According to an example embodiment of the present disclosure, the profile analyzer 603 may generate a user profile based on user data received from the wear device and may store the user profile in a profile storage unit 605*b* of the storage unit 605 to correspond to the identification information detected through an authentication operation in the authentication unit 602. The profile analyzer may be realized, for example, and without limitation by processing circuitry, such as, for example, and without limitation, a processor, dedicated processor, application-specific integrated circuit, field-programmable gate array (FPGA), logic circuitry, application processor, or the like, executing program instructions.

According to an example embodiment of the present disclosure, the profile analyzer 603 may gather user data received from the wear device and may generate, based on the gathered user data, demography information, physical profile information (e.g., per-body part measure, muscular amount, and exercise record), bio profile information (e.g., ECG pattern, blood pressure, or body temperature), and mental profile information (e.g., emotional state (happy, gloomy, or sad) and stable/unstable state).

According to an example embodiment of the present disclosure, the service providing unit 604 may detect service information corresponding to the identification information regarding the user wearing the wear device and provide the service information to the wear device. The service providing unit may be realized, for example, and without limitation by processing circuitry, such as, for example, and without limitation, a processor, dedicated processor, application-specific integrated circuit, field-programmable gate array (FPGA), logic circuitry, application processor, or the like, executing program instructions.

According to an example embodiment of the present disclosure, after the authentication of the user wearing the wear device is done through the authentication operation of the authentication unit 602, upon reception of configuration information regarding the wear device from the wear device, the service providing unit 604 may detect service information corresponding to the configuration information regarding the wear device and transmit the detected service information to the wear device. The configuration information on the wear device may include specification information (e.g., capacity of storage unit or whether a display is present) on hardware included in the wear device and sensor information.

According to an example embodiment of the present disclosure, the service providing unit 604 may provide an application list corresponding to the configuration information regarding the wear device to the wear device or an electronic device connected with the wear device. Upon receiving information (e.g., an application ID) regarding an application selected from the wear device or the electronic device connected with the wear device, the service providing unit 604 may detect an application corresponding to the application information received from the wear device among applications stored in an application storage unit 605c of the storage unit 605 and transmit the application to the wear device.

According to an example embodiment of the present disclosure, the service providing unit 604 may provide a customized service (e.g., type of exercise, settings of exercise equipment, clothing recommendation, cheer-up service, coaching service, advertisement service, or find missing children service) to the wear device based on the configuration information on the wear device and the user profile corresponding to the identification information regarding the user wearing the wear device.

According to an example embodiment of the present disclosure, the storage unit 605 may include the authentication information storage unit 605a storing at least one piece of authentication information respectively corresponding to a plurality of identification information, the profile storage unit 605b storing user profile information corresponding to each of a plurality of identification information, and the application storage unit 605c storing a plurality of applications. Further, the storage unit 605 may include service information corresponding to each of the plurality of identification information. Further, the storage unit 605 may include service information corresponding to configuration information regarding the wear device that is received from the wear device.

According to an example embodiment of the present disclosure, the authentication information storage unit 605a may store at least one piece of bio information (e.g., ECG signal or heart rate signal) corresponding to identification information, as authentication information.

According to an example embodiment of the present disclosure, the wear device 103 detects authentication information regarding the user wearing the wear device in a first state and transmits the authentication information to the server, and when the authentication of the user is done through the server, the wear device 103 detects user data of the wear device in a second state and transmits the user data to the server. The server 105 includes a server that, upon detection of the user's identification information using the authentication information received from the wear device, completes the user authentication, generates a user profile based on the user data received from the wear device, stores the user profile to correspond to the identification information, and provides service information related to the user to the wear device.

According to an example embodiment of the present disclosure, the wear device 103 may include a first controller detecting the authentication information and wearing the wear device using at least one sensor among a plurality of sensors in the first state which is a low-power, standby state, and when the authentication of the user is complete, waking up a second controller and switching into a sleep state, the second controller in the second state detecting the user data of the wear device using the plurality of sensors, upon detecting taking off the wear device using the at least one sensor, waking up the first controller and switching into the sleep state, a power manager controlling a power supply to supply power, and the plurality of sensors for detecting the wearing and taking off the wear device, the authentication information, and the user data.

According to an example embodiment of the present disclosure, the at least one sensor of the plurality of sensors may detect a bio signal of the user wearing the wear device, and the authentication information may include the bio signal of the user.

According to an example embodiment of the present disclosure, the wear device 103 may perform an operation of authenticating the user through the server using an electronic device connected with the wear device, transmit the user data to the server, and receive service information related to the user from the server.

According to an example embodiment of the present disclosure, the server 105 may include an authentication unit transmitting authentication complete information to the wear device when detecting identification information stored corresponding to the authentication information received from the wear device among a plurality of identification information stored in a storage unit of the server, a profile analyzer generating a user profile based on the user data received from the wear device, a service providing unit detecting service information corresponding to the identification information and providing the service information to the wear device, and the storage unit storing the authentication information corresponding to the identification information, the user profile information corresponding to the identification information, the service information, and a plurality of applications.

According to an example embodiment of the present disclosure, when receiving first authentication information from the wear device worn by the user with the user's identification information generated by an electronic device connected using the generated identification information, the server 105 may register the first authentication information as new authentication information corresponding to the identification information, and when, upon receiving second authentication information from another wear device worn by the user, the second authentication information received from the other wear device is not present as authentication information corresponding to the identification information, register the second authentication information as additional authentication information corresponding to the identification information.

According to an example embodiment of the present disclosure, the first authentication information and the second authentication information may represent different types of bio information.

According to an example embodiment of the present disclosure, the wear device 103, upon completing the authentication of the user through the server, may transmit configuration information regarding the wear device to the server and receive service information corresponding to the configuration information regarding the wear device from the server.

According to an example embodiment of the present disclosure, the service information corresponding to the configuration information regarding the wear device may include at least one application available on the wear device.

According to an example embodiment of the present disclosure, the wear device 103 may, when not in communication connection with the server, store the user data in the wear device or an electronic device connected via communication with the wear device, and when establishing a communication connection with the server, transmit the user data stored in the wear device or the electronic device to the server to be synced.

Figure 7:
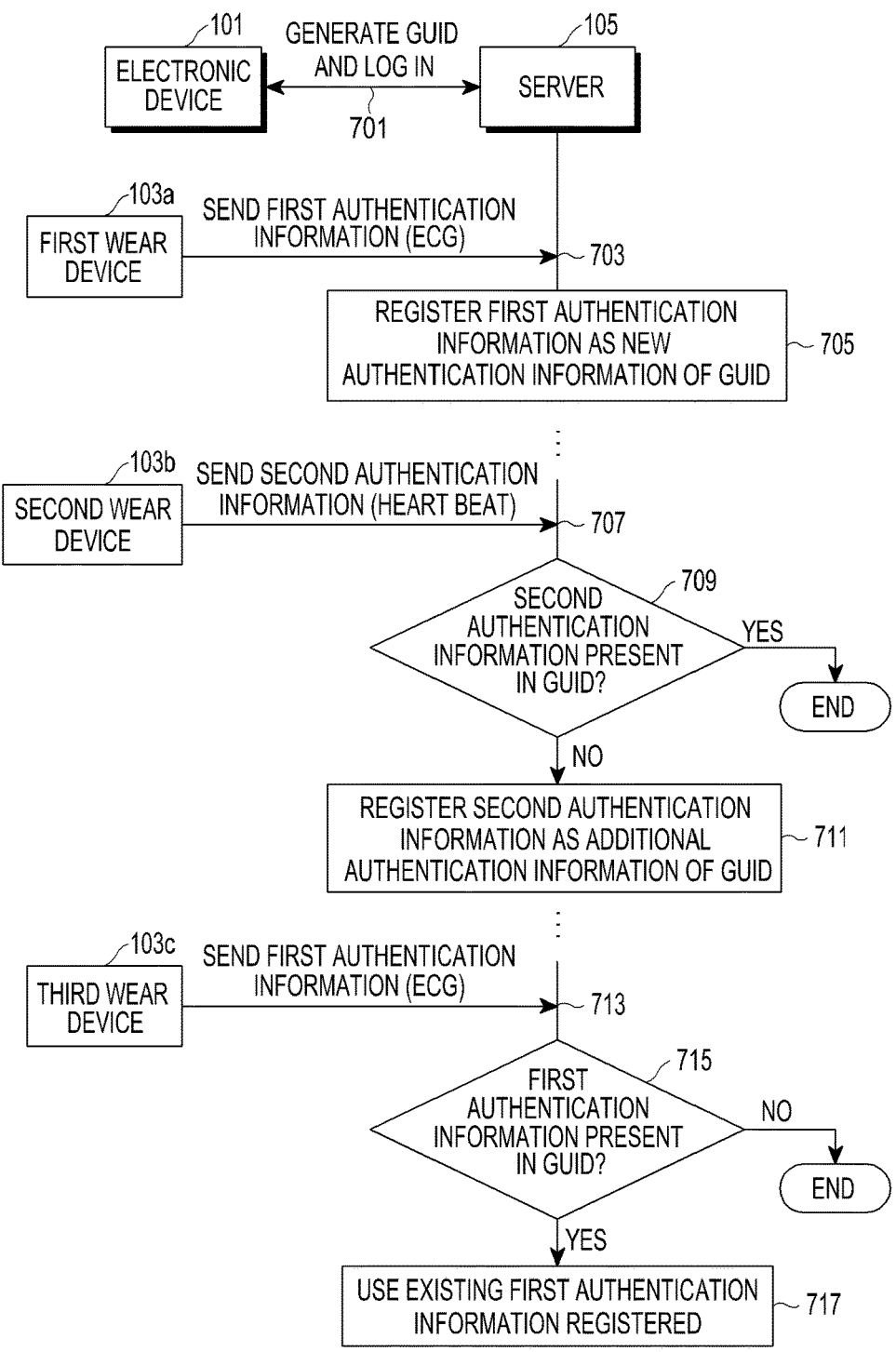
FIG. 7 is a flowchart illustrating an example method for registering authentication information in a wear system for providing services according to an example embodiment of the present disclosure

FIG. 7 is a flowchart illustrating an example method for registering authentication information in a wear system for providing services according to an example embodiment of the present disclosure. The authentication information registration method according to an example embodiment as illustrated in FIG. 7 may be performed in the wear system 100 of FIG. 1, for example.

Referring to FIG. 7, in operation 701, the user may access the server through the electronic device 101, generate new identification information (e.g., a GUID) for identifying the user, and log into the server 105 using the new identification information.

In operation 703, while the electronic device 101 remains logging in the server 105, a first wear device 103a worn by the user may transmit first authentication information output through a first authentication sensor of the first wear device 103a to the server 105. For example, when the first wear device 103a includes an ECG sensor as the authentication sensor, the first wear device 103a may transmit the user's ECG signal to the server 105 as first authentication information.

In operation 705, the server 105 may store the first authentication information received from the first wear device 103a as new authentication information corresponding to the identification information.

In operation 707, while the electronic device 101 remains logging in the server 105, a second wear device 103b worn by the user may transmit second authentication information output through a second authentication sensor of the second wear device 103b to the server 105. For example, when the second wear device 103b includes a heartbeat sensor as the authentication sensor, the second wear device 103b may transmit the user's heartbeat signal to the server 105 as second authentication information.

In operation 709, the server 105, upon receiving the second authentication information from the second wear device 103b, may determine whether second authentication information of the same type is among pieces of authentication information corresponding to the identification information. When it is determined that the same type of second authentication information is not among the pieces of authentication information corresponding to the identification information, the server 105, in operation 711, may store the second authentication information received from the second wear device 103b as additional authentication information corresponding to the identification information.

In operation 713, while the electronic device 101 remains logging in the server 105, a third wear device 103c worn by the user may transmit first authentication information outputted through a first authentication sensor of the third wear device 103c to the server 105. For example, when the third wear device 103c includes an ECG sensor as the authentication sensor, the third wear device 103c may transmit the user's ECG signal to the server 105 as first authentication information.

In operation 715, the server 105, upon receiving the first authentication information from the third wear device 103c, may determine whether first authentication information of the same type is among pieces of authentication information corresponding to the identification information. When it is determined that the same type of first authentication information is among the pieces of authentication information corresponding to the identification information, the server 105, in operation 717, uses the existing first authentication information corresponding to the identification information.

By the operations illustrated in FIG. 7, the authentication information storage unit (e.g., the authentication information storage unit 605a) of the storage unit in the server may store a plurality of identification information as illustrated in FIG. 8.

FIG. 8 is a diagram illustrating example authentication information in a server according to an example embodiment of the present disclosure. As illustrated in FIG. 8, the server may include a plurality of identification information (e.g., GUID 810) and at least one authentication information 820a to 820c corresponding to each of the plurality of identification information 810. At least one piece of authentication information corresponding to one piece of identification information may include different types of bio information.

For example, for first identification information 810a, an ECG signal 820a and fingerprint signal 820c are stored as authentication information, for second identification information 810b, a heartbeat waveform signal 820b is stored as authentication information, and for third identification information 810c, a heartbeat waveform signal 820b and fingerprint signal 820c are stored as authentication information.

Figure 9:
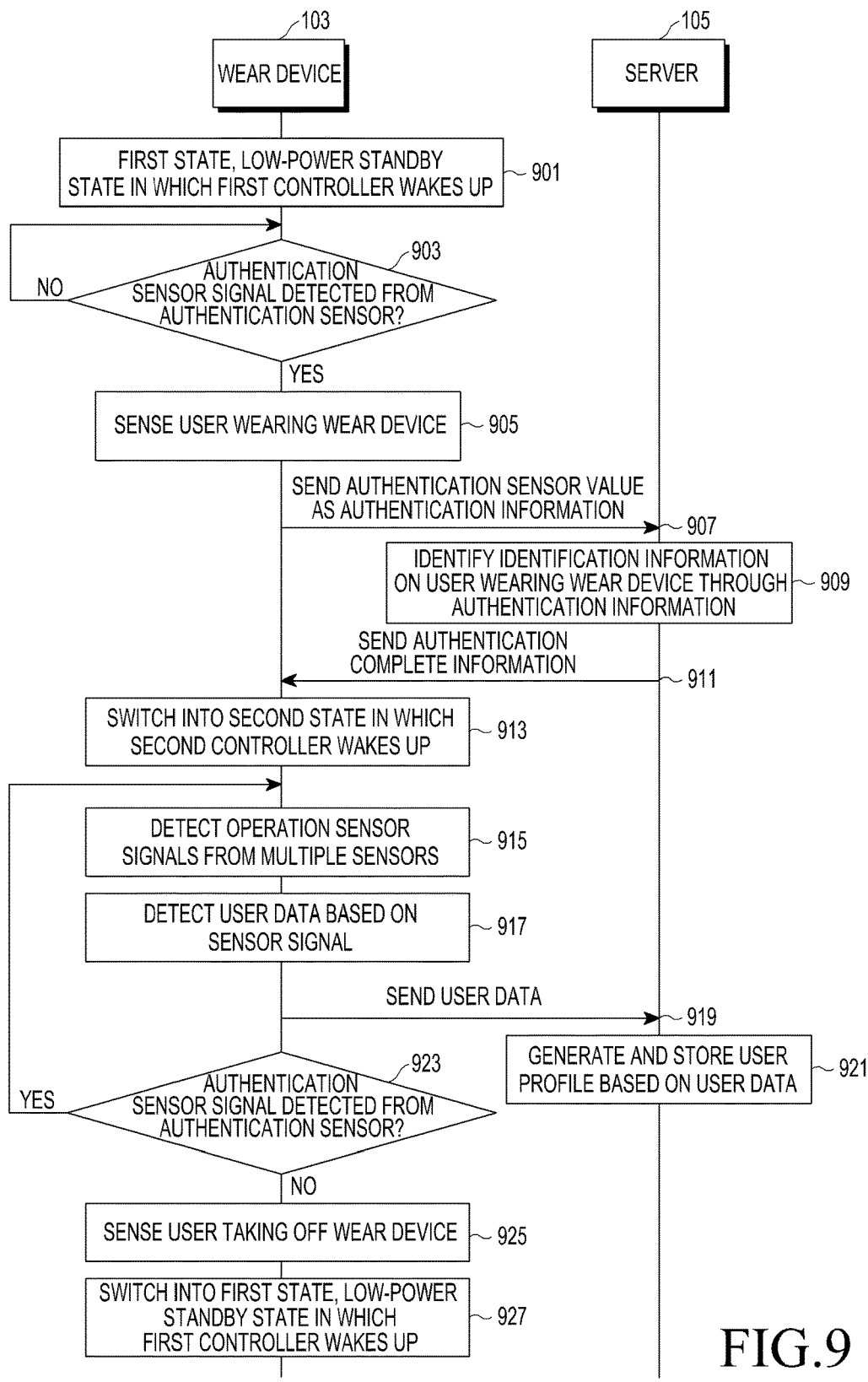
FIG. 9 is a flowchart illustrating an example method for gathering user data in a wear system for providing services according to an example embodiment of the present disclosure.

FIG. 9 is a flowchart illustrating an example method for gathering user data in a wear system for providing services according to an example embodiment of the present disclosure. The user data gathering method according to an example embodiment as illustrated in FIG. 9 may be performed in the wear system 100 of FIG. 1, for example. Although data transmission/reception through direct communication between a wear device and a server is described as an example in connection with FIG. 9, data transmission/reception between the wear device and the server may also be possible through an electronic device connected via communication with the wear device.

Referring to FIG. 9, in operation 901, the first controller in the wear device 103 may periodically wake up in a first state which is a low-power, standby state, determining whether to output an authentication sensor signal from at least one authentication sensor of the wear device 103.

When detecting an authentication sensor signal from the authentication sensor in operation 903, the first controller may sense the user wearing the wear device 103 in operation 905. In operation 907, the first controller may transmit the authentication sensor signal detected in operation 903, as authentication information, to the server 105.

In operation 909, upon reception of the authentication information from the wear device 103, the server 105 may determine whether the authentication information received from the wear device 103 is among at least one piece of authentication information respectively corresponding to a plurality of identification information stored in the storage unit of the server 105. The server 105, when the storage unit of the server has the authentication information received from the wear device 103, may detect identification information corresponding to the authentication information.

In operation 911, the server 105 may transmit authentication complete information to the wear device 103.

In operation 913, upon reception of the authentication complete information from the server 105, the first controller of the wear device 103 wakes up the second controller of the wear device 103 and switches into a second state where the first controller turns into the sleep state.

In operation 915, the second controller may detect sensor signals outputted from at least one authentication sensor and at least one motion sensor of the wear device 103.

In operation 917, the second controller may generate sensor information including the type of sensor, sensor signal value, and context (e.g., position of sensor and time sensor signal is detected) based on the detected sensor signal and may detect user data of the wear device 103 based on the sensor information.

In operation 919, the second controller may transmit the detected user data to the server 105.

In operation 921, the server 105 may generate a user profile based on the user data received from the wear device 103 and may store the user profile to correspond to the identification information identified in operation 909.

In operation 923, upon detecting the authentication sensor signal from the authentication sensor of the wear device 103, the second controller may repeat operations 915 to 919 while transmitting the user data of the wear device to the server 105.

However, upon failing to receive the authentication sensor signal from the authentication sensor of the wear device 103 in operation 923, the second controller may sense the user taking off the wear device 103 in operation 925.

In operation 927, the second controller may wake up the first controller and switch into the first state, a low-power standby state, where the second controller turns into the sleep state.

Figure 10:
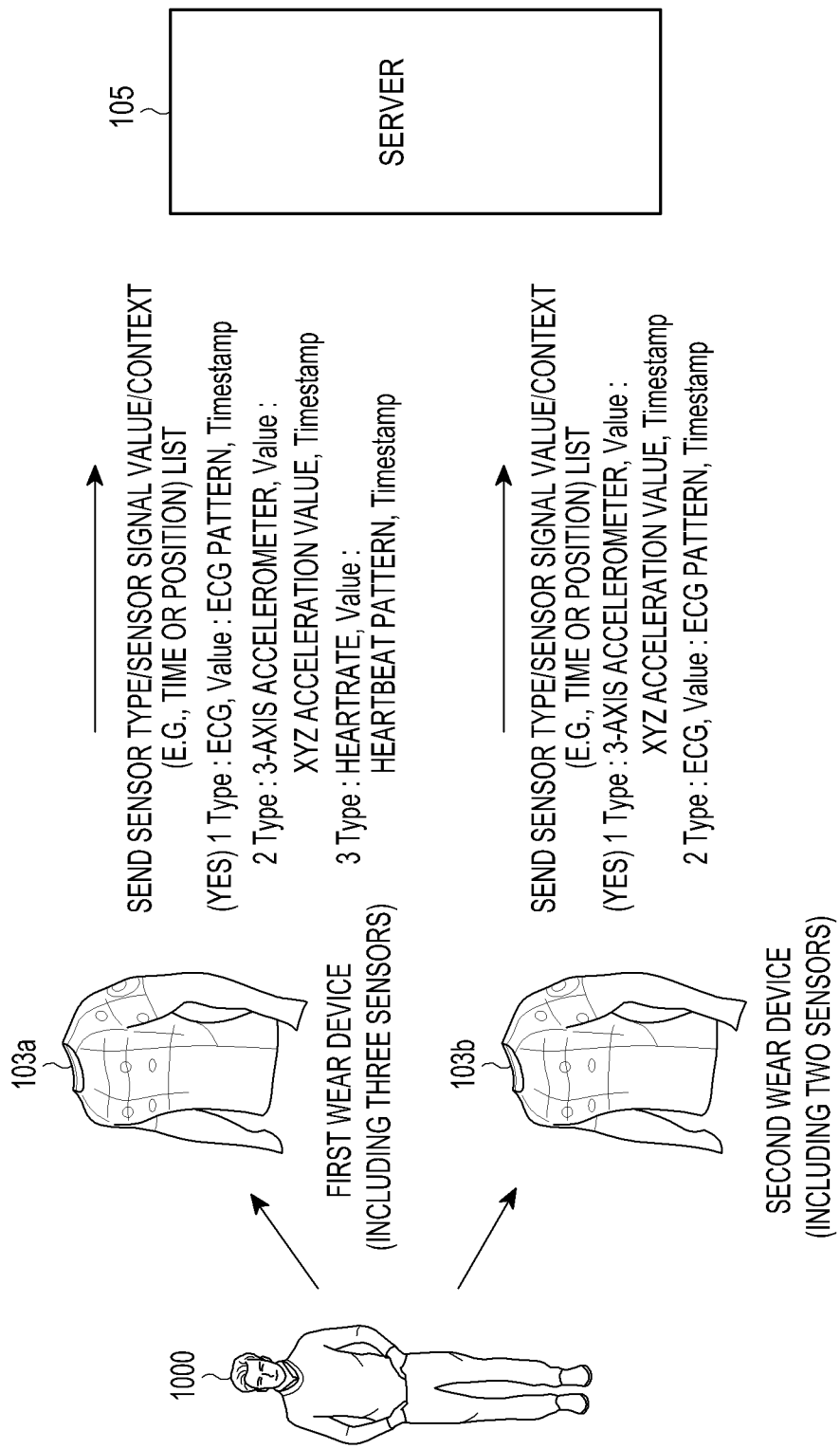
FIG. 10 is a diagram illustrating example operations of generating data by a user on a wear device according to an example embodiment of the present disclosure.

FIG. 10 is a diagram illustrating example operations of generating data by a user on a wear device according to an example embodiment of the present disclosure. The user data generation operations according to an example embodiment as illustrated in FIG. 10 may be performed in the wear system 100 of FIG. 1, for example.

As illustrated in FIG. 10, when sensor values are output from three sensors (e.g., an ECG sensor, acceleration sensor, and heartbeat sensor) equipped in the first wear device 103*a*, with authentication of the user 1000 wearing the first wear device 103*a* completed through the server 105, the first wear device 103*a* may generate, as user data, sensor information including the sensor type, sensor signal value, and context (e.g., position of sensor and time sensor signal is detected) for each of the three sensors.

For example, when the first wear device 103*a* includes an ECG sensor, an acceleration sensor, and a heartbeat sensor, the first wear device 103*a* may generate user data including sensor information for the ECG sensor (type 1) including a sensor type (ECG), sensor signal value (Value, ECG pattern), and context (Time stamp), sensor information for the acceleration sensor (type 2) including a sensor type (three-axis acceleration), sensor signal value (Value, XYZ acceleration value), and context (Time stamp), and sensor information for the heartbeat sensor (type 3) including a sensor type (heartbeat sensor), sensor signal value (Value, heart-rate), and context (Time stamp) and transmit the user data to the server 105.

Further, when sensor values are output from two sensors (e.g., an acceleration sensor and heartbeat sensor) equipped in the second wear device 103*b*, with authentication of the user 1000 wearing the second wear device 103*b* completed through the server 105, the second wear device 103*b* may generate, as user data, sensor information including the sensor type, sensor signal value, and context (e.g., position of sensor and time sensor signal is detected) for each of the two sensors.

For example, when the second wear device 103*b* includes an acceleration sensor and an ECG sensor, the second wear device 103*b* may generate user data including sensor information for the acceleration sensor (type 1) including a sensor type (three-axis acceleration), sensor signal value (Value, XYZ acceleration value), and context (Time stamp) and sensor information for the ECG sensor (type 2) including a sensor type (ECG), sensor signal value (Value, ECG pattern), and context (Time stamp) and transmit the user data to the server 105.

Figure 11:
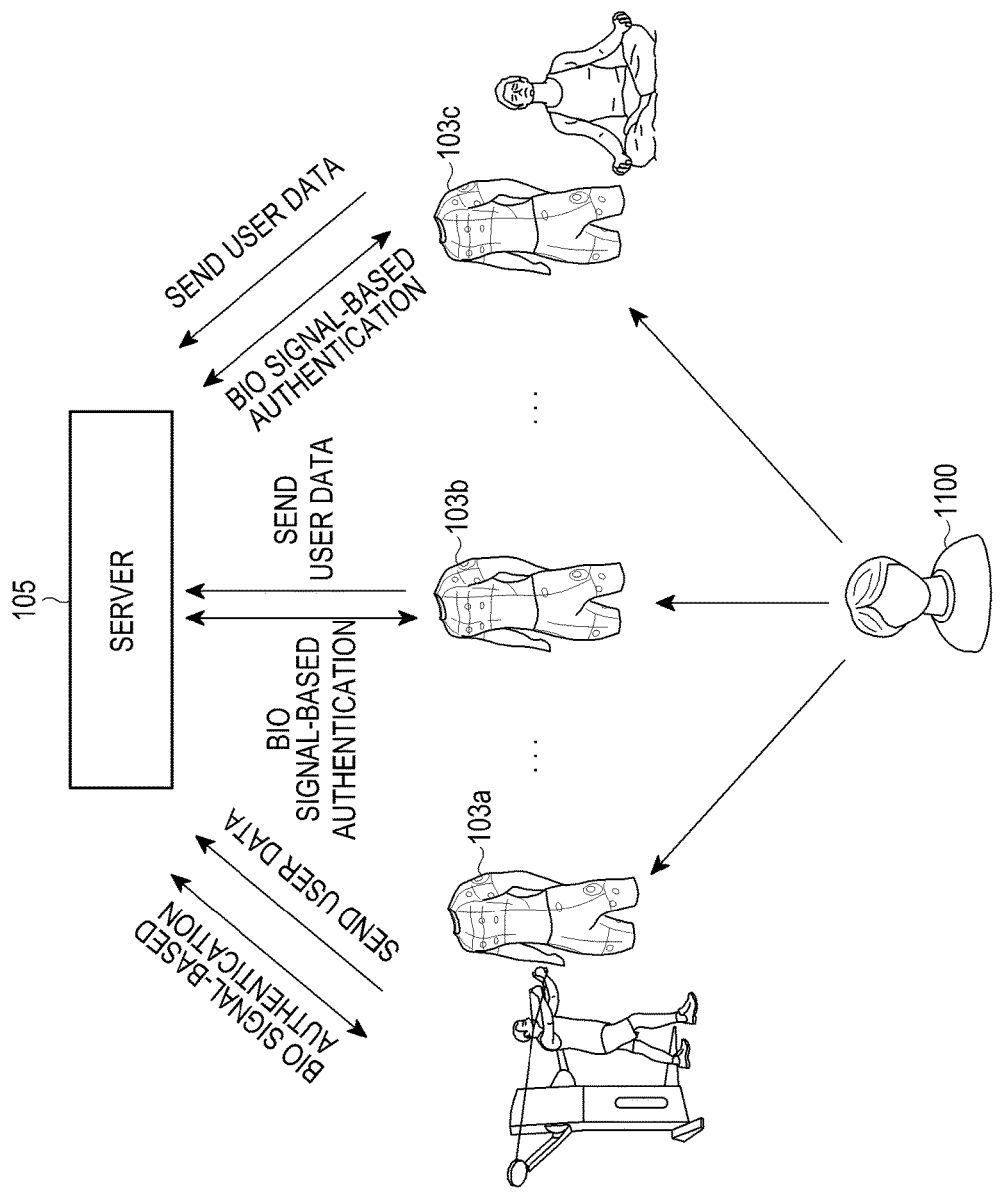
FIG. 11 is a diagram illustrating an example data management operation by a user on a wear system for providing services according to an example embodiment of the present disclosure

FIG. 11 is a diagram illustrating an example data management operation by a user on a wear system for providing services according to an example embodiment of the present disclosure. The user data management operation according to an example embodiment as illustrated in FIG. 11 may be performed in the wear system 100 of FIG. 1, for example.

As illustrated in FIG. 11, whenever or wherever the user 1100 wears any wear device, the user 1100 may be authenticated through the server 105 based on the user's bio signal, and user data generated through the wear device worn by the user 1100 may be sent to the server 105, allowing personal profile data of the user 1100 to be managed in an integrated manner.

For example, when the user 1100 wears the first wear device 103*a* provided in a fitness center, the user 1100 may be authenticated through the server 105 based on a bio signal of the user 1100, and user data generated through the first wear device 103*a* worn by the user 1100 may be sent to the server 105 to be stored as the user's personal profile data.

For example, when the user 1100 wears the second wear device 103*b* provided in another place, the user 1100 may be authenticated through the server 105 based on a bio signal of the user 1100, and user data generated through the second wear device 103*b* worn by the user 1100 may be sent to the server 105 to be stored as the user's personal profile data.

For example, when the user 1100 wears the third wear device 103*c* provided in a yoga class studio, the user 1000 may be authenticated through the server 105 based on a bio signal of the user 1100, and user data generated through the third wear device 103*b* worn by the user 1100 may be sent to the server 105 to be stored as the user's personal profile data.

Figure 12:
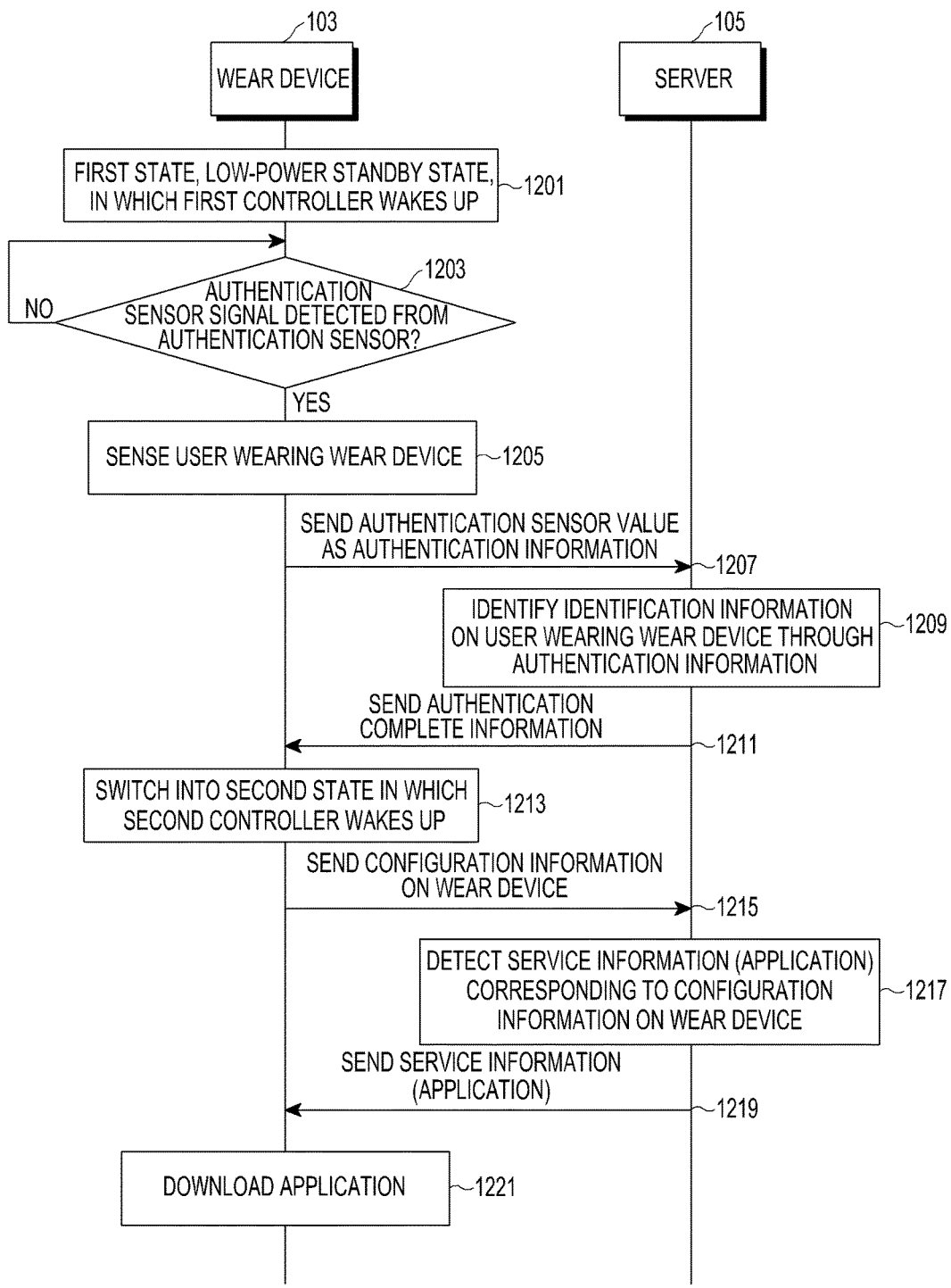
FIG. 12 is a flowchart illustrating an example method for providing service information in a wear system for providing services according to an example embodiment of the present disclosure

FIG. 12 is a flowchart illustrating an example method for providing service information in a wear system for providing services according to an example embodiment of the present disclosure. The service information providing method according to an example embodiment as illustrated in FIG. 12 may be performed in the wear system 100 of FIG.

1, for example. Although data transmission/reception through direct communication between a wear device and a server is described as an example in connection with FIG. 12, data transmission/reception between the wear device and the server may also be possible through an electronic device connected via communication with the wear device.

Referring to FIG. 12, in operation 1201, the first controller in the wear device 103 may periodically wake up in a first state which is a low-power, standby state, determining whether to output an authentication sensor signal from at least one authentication sensor of the wear device 103.

When detecting an authentication sensor signal from the authentication sensor in operation 1203, the first controller may sense the user wearing the wear device 103 in operation 1205. In operation 1207, the first controller may transmit the authentication sensor signal detected in operation 1203, as authentication information, to the server 105.

In operation 1209, upon reception of the authentication information from the wear device 103, the server 105 may determine whether the authentication information received from the wear device 103 is among at least one piece of authentication information respectively corresponding to a plurality of identification information stored in the storage unit of the server 105. The server 105, when the storage unit of the server has the authentication information received from the wear device 103, may detect identification information corresponding to the authentication information.

In operation 1211, the server 105 may transmit authentication complete information to the wear device 103.

In operation 1213, upon reception of the authentication complete information from the server 105, the first controller of the wear device 103 wakes up the second controller of the wear device 103 and switches into a second state where the first controller turns into the sleep state.

In operation 1215, the second controller may transmit configuration information (e.g., sensor information or hardware specification information) regarding the wear device 101 to the server 105.

In operation 1217, upon receiving the configuration information regarding the wear device from the wear device 103, the server 105 may detect service information (e.g., an application) corresponding to the configuration information regarding the wear device.

In operation 1219, the server may transmit the service information (e.g., an application available on the wear device) corresponding to the configuration information regarding the wear device to the wear device 103.

In operation 1221, the second controller may download an application received from the server 105 onto the storage unit of the wear device.

Or, the server 105 may detect a list of applications available on the wear device, as service information corresponding to the configuration information regarding the wear device, and transmit the list to the wear device 103. The wear device 103 may display the application list received from the server 105 on the display of the wear device 103 and transmit information (e.g., an application ID) regarding an application selected by the user's touch to the server 105. The server 105 may provide an application corresponding to the application information received from the wear device 103 to the wear device 103.

The second controller may run the downloaded application to display on the display of the wear device 103 while outputting a corresponding audio through a speaker (not shown) of the wear device 103.

Further, when the wear device 103 separately establishes a communication connection with the electronic device after downloading the application, the second controller may run the application through the electronic device.

Although the operation of receiving a service through direct communication between the wear device 103 and the server 105 is described in connection with FIG. 12, the wear device 103 may also receive service information from the server 105 through the electronic device. Data transmission and reception between the wear device and the server using the electronic device are described below in connection with FIG. 13.

Figure 13:
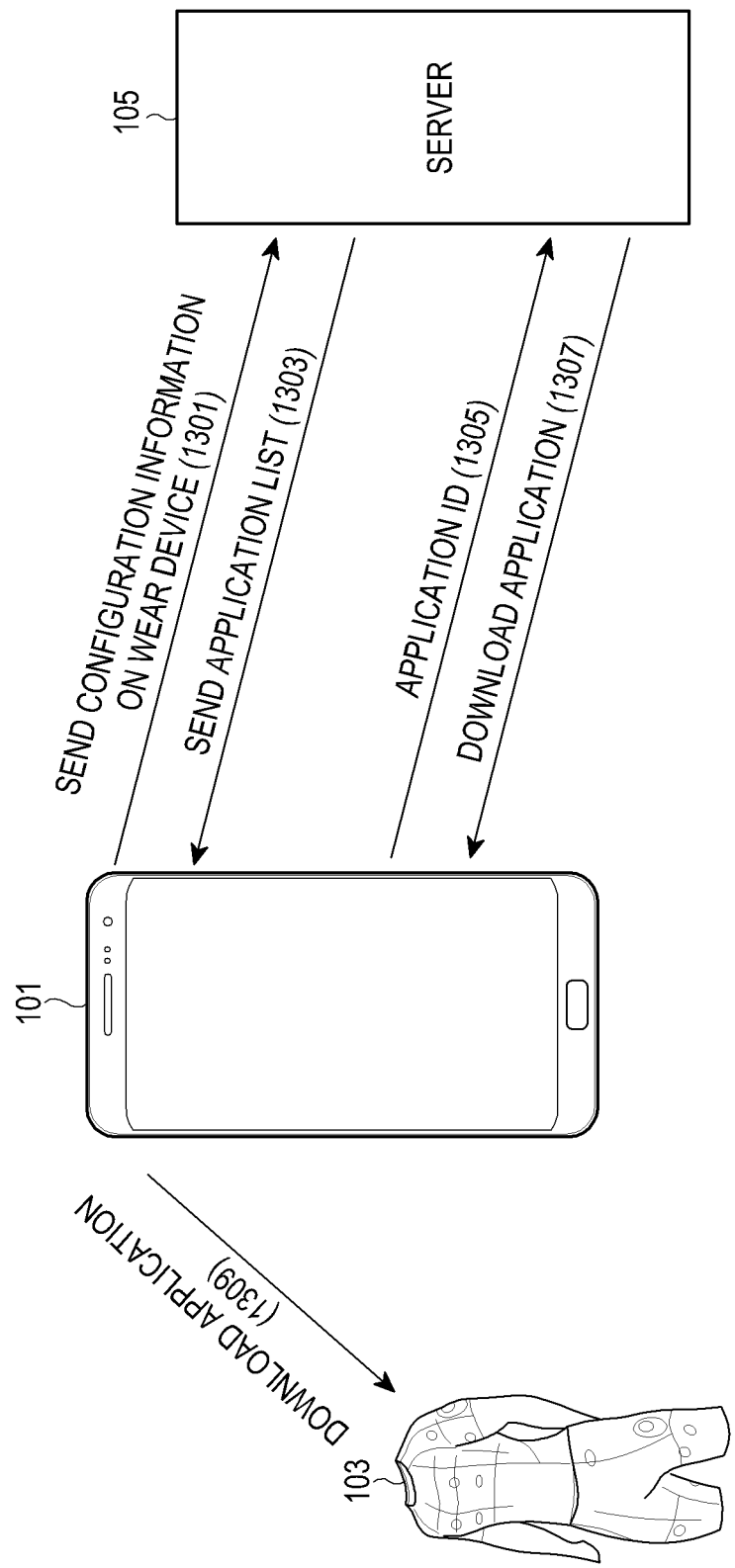
FIG. 13 is a diagram illustrating an example operation for providing service information through an electronic device in a wear system for providing services according to an example embodiment of the present disclosure

FIG. 13 is a diagram illustrating an example operation for providing service information through an electronic device in a wear system for providing services according to an example embodiment of the present disclosure. The service information providing method according to an example embodiment as illustrated in FIG. 13 may be performed in the wear system 100 of FIG. 1, for example.

Referring to FIG. 13, the wear device 103 worn by the user is in short-range communication connection with the electronic device 101, and the wear device 103 has completed its authentication by transmitting the user's authentication information to the server 105 via the electronic device 101.

In operation 1301, the electronic device 101 may transmit configuration information (e.g., sensor information or hardware specification information) regarding the wear device received from the wear device 103 to the server 105.

In operation 1303, the server 105 may generate service information compatible with the wear device, e.g., an application list, based on the configuration information (e.g., sensor information or hardware specification) regarding the wear device and transmit the service information to the electronic device 101.

In operation 1305, the electronic device may display the application list received from the server 105 on the display of the electronic device, and when a predetermined application is selected from the application list by the user, the electronic device 101 may transmit information (ID) regarding the selected application to the server 105.

In operation 1307, the server 105 may detect an application corresponding to the application information (ID) received from the electronic device 101 from the application storage unit of the storage unit of the server and transmit the application to the electronic device 101.

In operation 1309, the electronic device 101 may transmit the application downloaded from the server to the wear device 1009.

FIG. 14 is a diagram illustrating example service information provided from a server according to an example embodiment of the present disclosure. As illustrated in FIG. 14, the storage unit of the server may store service information 1401 corresponding to configuration information 1403 and 1405 regarding the wear device.

For example, when the configuration information regarding the wear device includes information on sensors including a touch sensor, ECG sensor, EMG sensor, and heartbeat sensor and a specification of hardware including a 2GM RAM and display, the server may provide an advertisement service 1401a to the wear device.

For example, when the configuration information regarding the wear device includes information on sensors including an acceleration sensor, ECG sensor, and EMG sensor and a specification of hardware including a 2GM RAM, the server may provide a personalized fitness service 1401b to the wear device.

Figure 15:
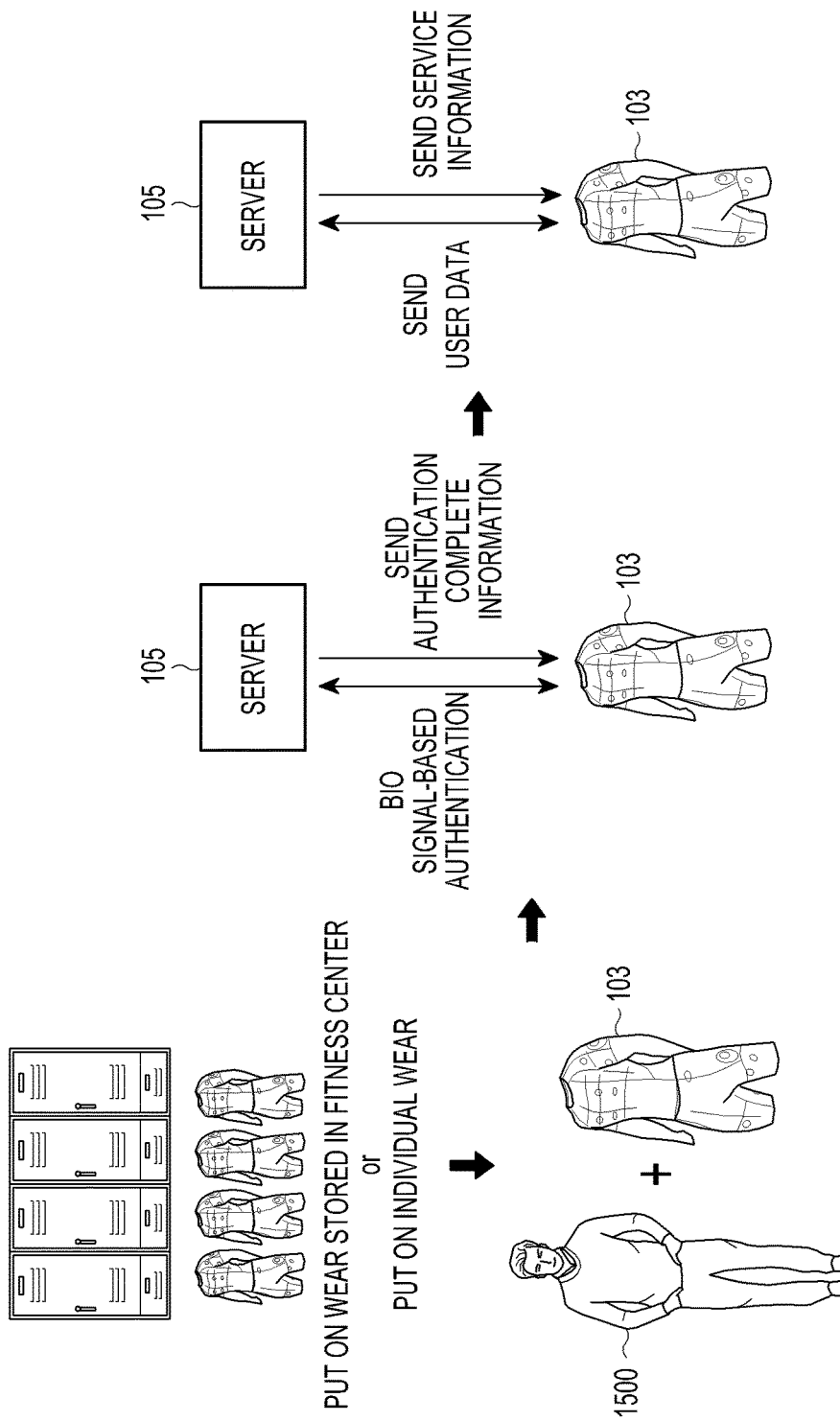
FIGS. 15A, 15B and 15C are diagrams illustrating an example of providing a service in a wear system for providing services according to an example embodiment of the present disclosure.

FIGS. 15A, 15B and 5C are diagrams illustrating an example of providing a service in a wear system for providing services according to an example embodiment of the present disclosure. The service provision according to an example embodiment as illustrated in FIG. 15 may be performed in the wear system 100 of FIG. 1, for example.

As illustrated in FIG. 15A, the user 1500 may wear any one of a plurality of wear devices provided in a fitness center or his personal wear device as provided in the fitness center.

As illustrated in FIG. 15B, when the user 1500 wears the wear device 103, the wear device 103 may transmit authentication information including the user's bio signal to the server 105 and receive authentication complete information from the server 105.

As illustrated in FIG. 15C, when the authentication of the user 1500 is complete, upon sensing user data of the wear device 103 to the server 105, the server 105 may generate a profile (e.g., information such as load, part, and place of exercise) of the user 1400 based on the user data of the wear device 103. The server 105 may manage information regarding the user's exercise history and use of exercise equipment in an integrated manner depending on the place or type of exercise by storing the user profile to correspond to the user's identification information. Further, the server may provide a load and part of exercise for a new exercise, as service information, to the wear device 103 based on a past exercise history.

Figure 16:
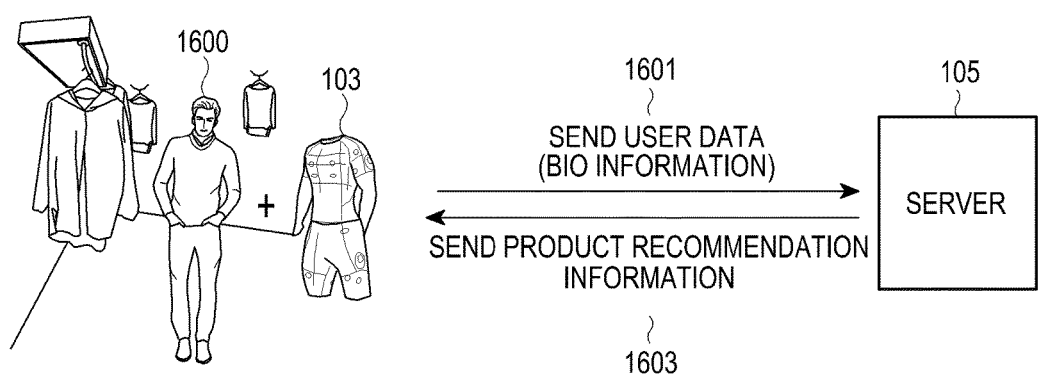
FIG. 16 is a diagram illustrating an example of providing a service in a wear system for providing services according to an example embodiment of the present disclosure.

FIG. 16 is a diagram illustrating an example of providing a service in a wear system for providing services according to an example embodiment of the present disclosure. The service provision according to an example embodiment as illustrated in FIG. 16 may be performed in the wear system 100 of FIG. 1, for example.

As illustrated in FIG. 16, when the user 1600 wearing the wear device 103 is located in a clothing shop with the authentication of the user 1600 complete through the server 105, the wear device 103, in operation 1601, may transmit, to the server 105, user data including bio information regarding the user 1600 detected using an authentication sensor detecting a bio signal and location information detected using a location sensor. The server 105 may notice that the user is currently in the clothing shop based on the location information of the user data received from the wear device 103 and may generate a user profile including, e.g., the user's body features and body constitution, based on the bio information of the user data. In operation 1603, the server 105 may receive information about clothes in the clothing shop from another server associated with the clothing shop, detect information about clothes fitting the user's body features and body constitution among the clothes in the clothing shop, and transmit the information, as product recommendation service information, to the wear device 103.

Figure 17A:
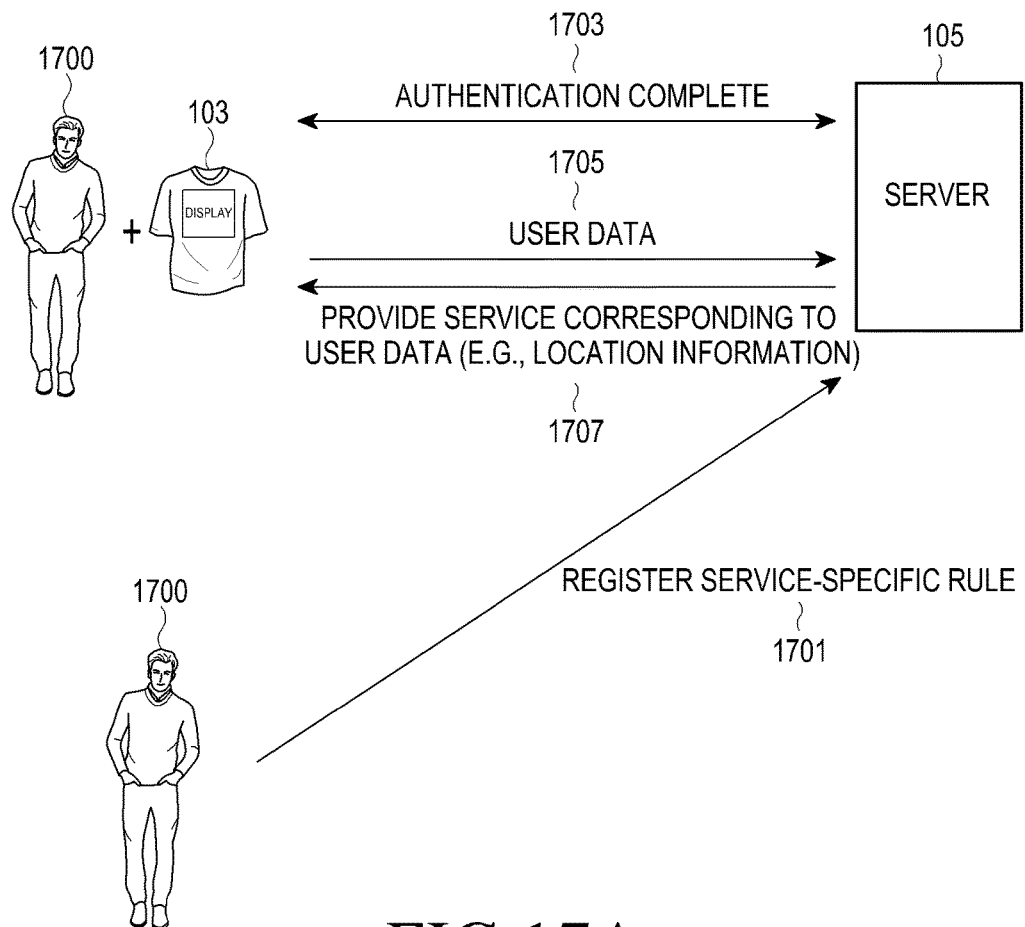
FIGS. 17A and 17B are diagrams illustrating other examples of providing a service in a wear system for providing services according to an example embodiment of the present disclosure.
Figure 17B:
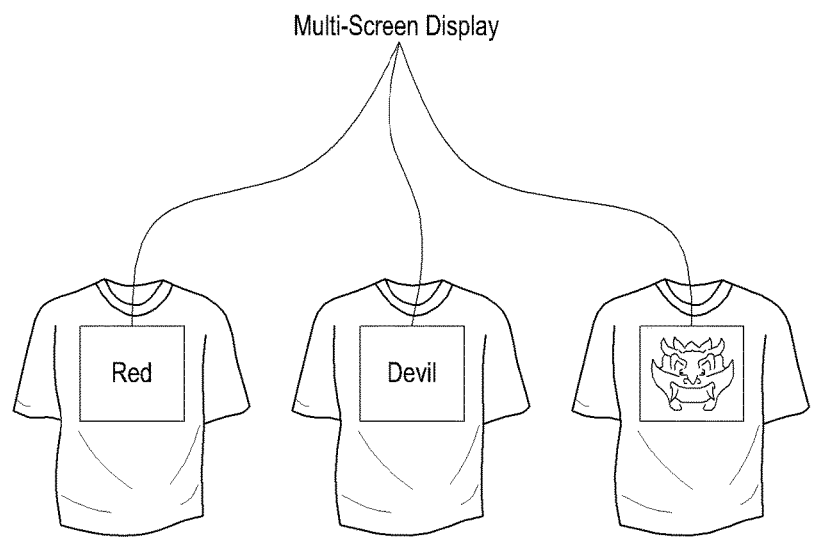

FIGS. 17A and 17B are diagrams illustrating other examples of providing a service in a wear system for providing services according to an example embodiment of the present disclosure. The service provision according to an example embodiment as illustrated in FIGS. 17A and 17B may be performed in the wear system 100 of FIG. 1, for example.

Referring to FIG. 17A, in operation 1701, a service-specific rule that when the user 1700 wearing the wear device accesses the server 150 through the electronic device and is located in a particular place (e.g., a play ground), a service (e.g., a cheerleading service for exercise) corresponding to the particular place may previously be registered in the server.

In operation 1703, the user 1700, after wearing the wear device 103, may complete his authentication through the server 105. In operation 1705, user data (e.g., location information) from the wear device 103 may be transmitted to the server 105.

In operation 1707, when the location information which is the user data received from the wear device 103 is identical with the location information corresponding to the service-specific rule, the server 105 may transmit service information corresponding to the information regarding the location of the user to the wear device 103.

For example, when the user 1700 previously registers a service-specific rule that he will receive, as a service, a cheerleading theme of the Red Devil supporters when arriving at the play ground, if the user 1700 wearing the wear device 103 gets to the play ground, it may receive group activity attendance session information or contents to be displayed on the display of the wear device 103 from the server 105. The group activity session information is information allowing the same or separate content to be transmitted to each of a plurality of wear devices divided into groups.

For example, when a service-specific rule that a plurality of users will receive, as a service, a cheerleading theme of the Red Devil supporters upon arriving at the play ground is previously registered in the server, and the plurality of users wearing wear devices are detected to be located in the same play ground, the server may transmit content corresponding to the cheerleading theme of the Red Devil supporters to the plurality of wear devices. Or, the server may split the content corresponding to the cheerleading theme of the Red Devil supporters using information about relative locations among the plurality of wear devices and may transmit the split contents to the plurality of wear devices, respectively.

As illustrated in FIG. 17B, the respective displays of the plurality of wear devices may simultaneously output the split contents received from the server.

Figure 19:
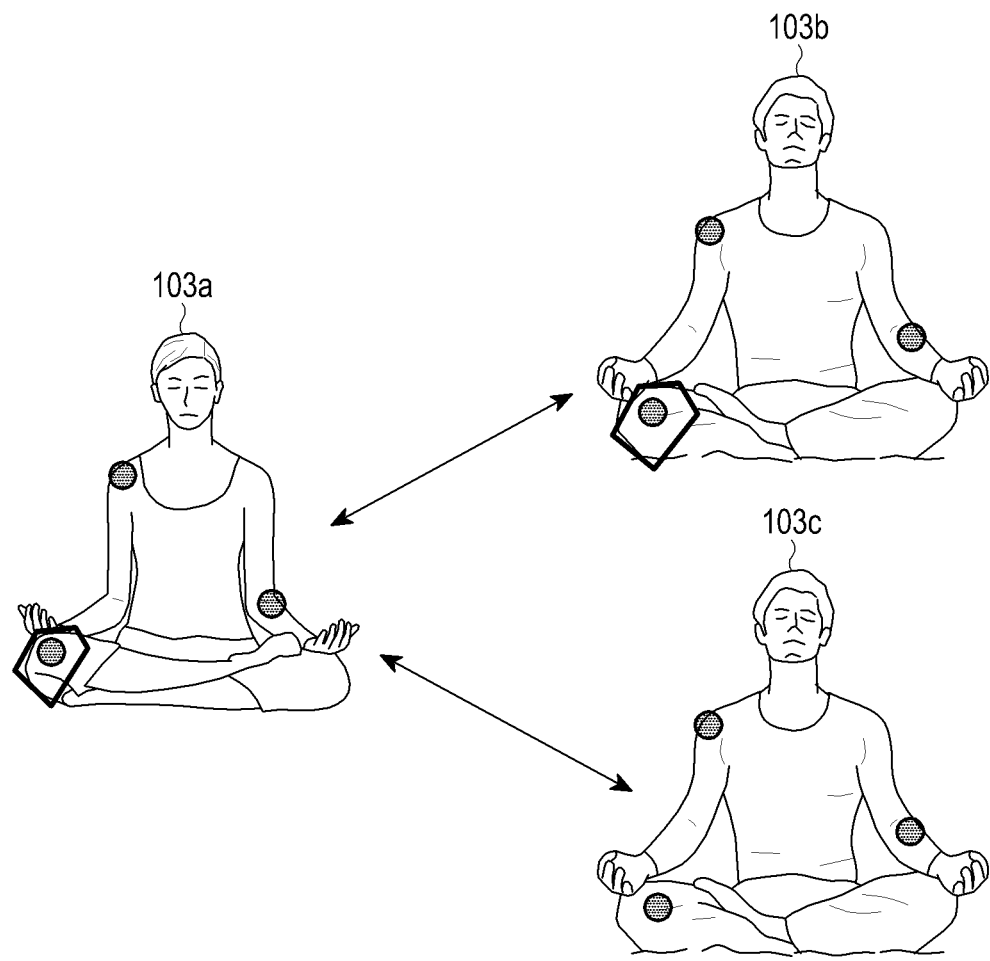
Figure 20:
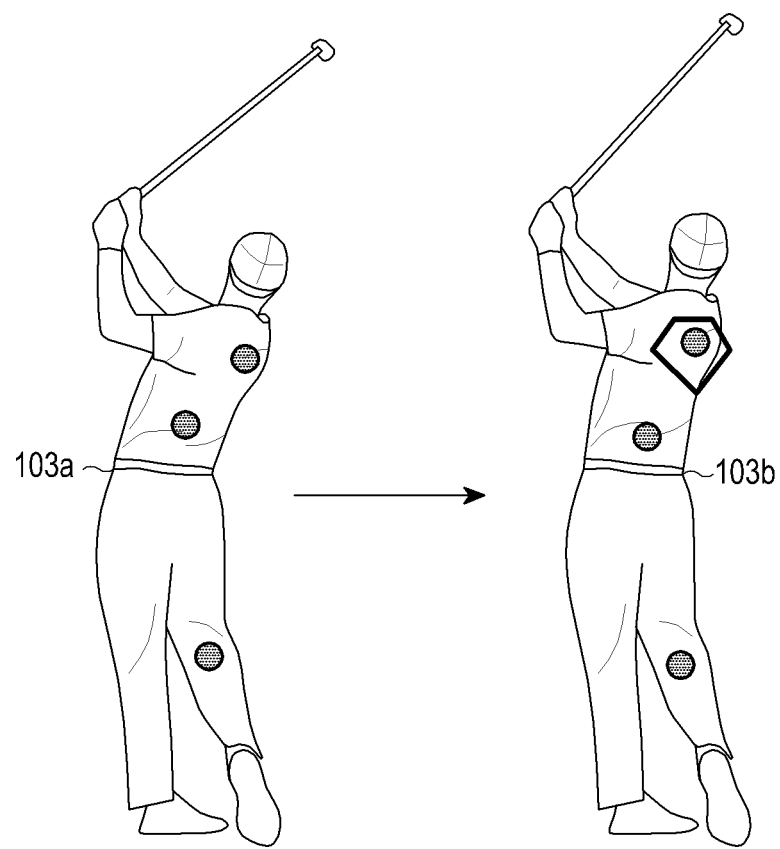

FIGS. 18A, 18B, 18C, 19 and 20 are diagrams illustrating other examples of providing a service in a wear system for providing services according to an example embodiment of the present disclosure. The service provision according to an example embodiment as illustrated in FIGS. 18 to 20 may be performed in the wear system 100 of FIG. 1, for example.

FIGS. 18A, 18B and 18C illustrate a real-time coaching service using the wear system.

As illustrated in FIG. 18A, when the user wearing the wear device 103a is authenticated as a coach through user authentication by the server, and the user wearing the second wear device 103b is authenticated as a trainee through user authentication by the server, user data detected from the first wear device 103a and the user data detected from the second wear device 103b may be transmitted to the server.

The server may compare the user data of the first wear device 103a with the user data of the second wear device 103b, and when unidentical sensor information is detected as a result of the comparison, the server may transmit the unidentical sensor information to at least one of the first wear device 103a and the second electronic device 103b.

When receiving sensor information from the server, the first wear device 103a may generate a vibration or light emission in a portion where the sensor corresponding to the received sensor information among the plurality of sensors of the first wear device 103a is positioned to alert the coach to the wrong exercise part of the trainee.

Further, the second wear device 103b may generate a vibration or light emission in a portion where the sensor corresponding to the sensor information received from the server among the plurality of sensors of the second wear device is positioned to allow the trainee himself to notice the wrong exercise part.

Transmission and reception of information between the first wear device 103a and the second wear device 103b may be performed via the server or directly in a peer-to-peer manner.

Further, as illustrated in FIG. 18B, a real-time, one-to-N coaching system may be performed using a wear system.

As illustrated in FIG. 18C, when a one-to-N coaching service is carried out, the first wear device 103a authenticated as a coach may receive sensor information corresponding to wrong parts of the trainees from the server, and a sensor corresponding to the sensor information received from the server among the plurality of sensors of the first wear device 103a may generate a vibration or light emission to alert the coach to the wrong parts of the trainees.

Further, when, among the plurality of wear devices 104 authenticated as trainees, the second wear device 104a receives the unidentical sensor information from the server, a vibration or light emission may be generated in a portion where the sensor corresponding to the sensor information received from the server among the plurality of sensors of the second wear device 104a is positioned, allowing the trainees themselves to notice the wrong exercise parts.

Transmission and reception of information between the first wear device 103a and the plurality of wear devices 104 may be performed via the server or directly in a peer-to-peer manner.

FIG. 19 is a diagram illustrating an example real-time yoga service using the wear system.

As illustrated in FIG. 19, when the user wearing the first wear device 103a is authenticated as a coach through user authentication by the server, and the user wearing the second wear device 103b and the user wearing the third wear device 103c are authenticated as trainees, respectively, through user authentication by the server, user data from the first wear device 103a and the user data from each of the second wear device 103b and the third wear device 103c may be transmitted to the server.

The server may compare the user data of the first wear device 103a with the user data of the second wear device 103b, and when unidentical sensor information is detected as a result of the comparison, the server may transmit the unidentical sensor information to the first wear device 103a and the second electronic device 103b. Further, the server may compare the user data of the first wear device 103a with the user data of the third wear device 103c, and when unidentical sensor information is detected as a result of the comparison, the server may transmit the unidentical sensor information to the first wear device 103a and the third electronic device 103c.

When receiving the unidentical service information from the server, the first wear device 103a may receive, together therewith, identification information allowing the user of the wear device where the unidentical sensor information has been generated to be identified.

Upon receiving the unidentical sensor information generated from the second wear device 103b, the first wear device 103a may generate a first vibration or first light emission in a portion where the sensor corresponding to the sensor information received from the server is positioned among the plurality of sensors of the first wear device 103a, alerting the coach to the wrong exercise part of the trainee wearing the second wear device 103b.

Or, upon receiving the unidentical sensor information generated from the third wear device 103c, the first wear device 103a may generate a second vibration distinct from the first vibration or second light emission distinct from the first light emission in a portion where the sensor corresponding to the sensor information received from the server is positioned among the plurality of sensors of the first wear device 103a, alerting the coach to the wrong exercise part of the trainee wearing the third wear device 103c.

Or, upon receiving the unidentical sensor information simultaneously generated from the second wear device 103b and third wear device 103c, the first wear device 103a may generate a third vibration distinct from the first and second vibration or third light emission distinct from the first and second light emission in an exercise portion where the sensor corresponding to the sensor information received from the server is positioned among the plurality of sensors of the first wear device 103a, alerting the coach to the wrong exercise parts of the trainees wearing the second wear device 103b and third wear device 103c.

Transmission and reception of information between the first wear device 103a and the plurality of wear devices 103b and 103c may be performed via the server or directly in a peer-to-peer manner.

FIG. 20 is a diagram illustrating an example real-time golf service using the wear system.

As illustrated in FIG. 20, when the user wearing the first wear device 103a is authenticated as a coach through user authentication by the server, and the user wearing the second wear device 103b is authenticated as a trainee through user authentication by the server, user data from the first wear device 103a and the user data from the second wear device 103b may be transmitted to the server.

The server may compare the user data of the first wear device 103a with the user data of the second wear device 103b, and when unidentical sensor information is detected, the server may transmit the unidentical sensor information to the first wear device 103a and the second electronic device 103b.

The first wear device 103a may generate a vibration or light emission in a portion where the sensor corresponding to the sensor information received from the server among the plurality of sensors of the first wear device 103a is positioned, alerting the coach to the wrong exercise part of the trainee.

Further, the second wear device 103b may generate a vibration or light emission in a portion where the sensor corresponding to the sensor information received from the server among the plurality of sensors of the second wear device is positioned to allow the trainee himself to notice the wrong part.

Transmission and reception of information between the first wear device 103a and the second wear device 103b may be performed via the server or directly in a peer-to-peer manner.

Figure 21A:
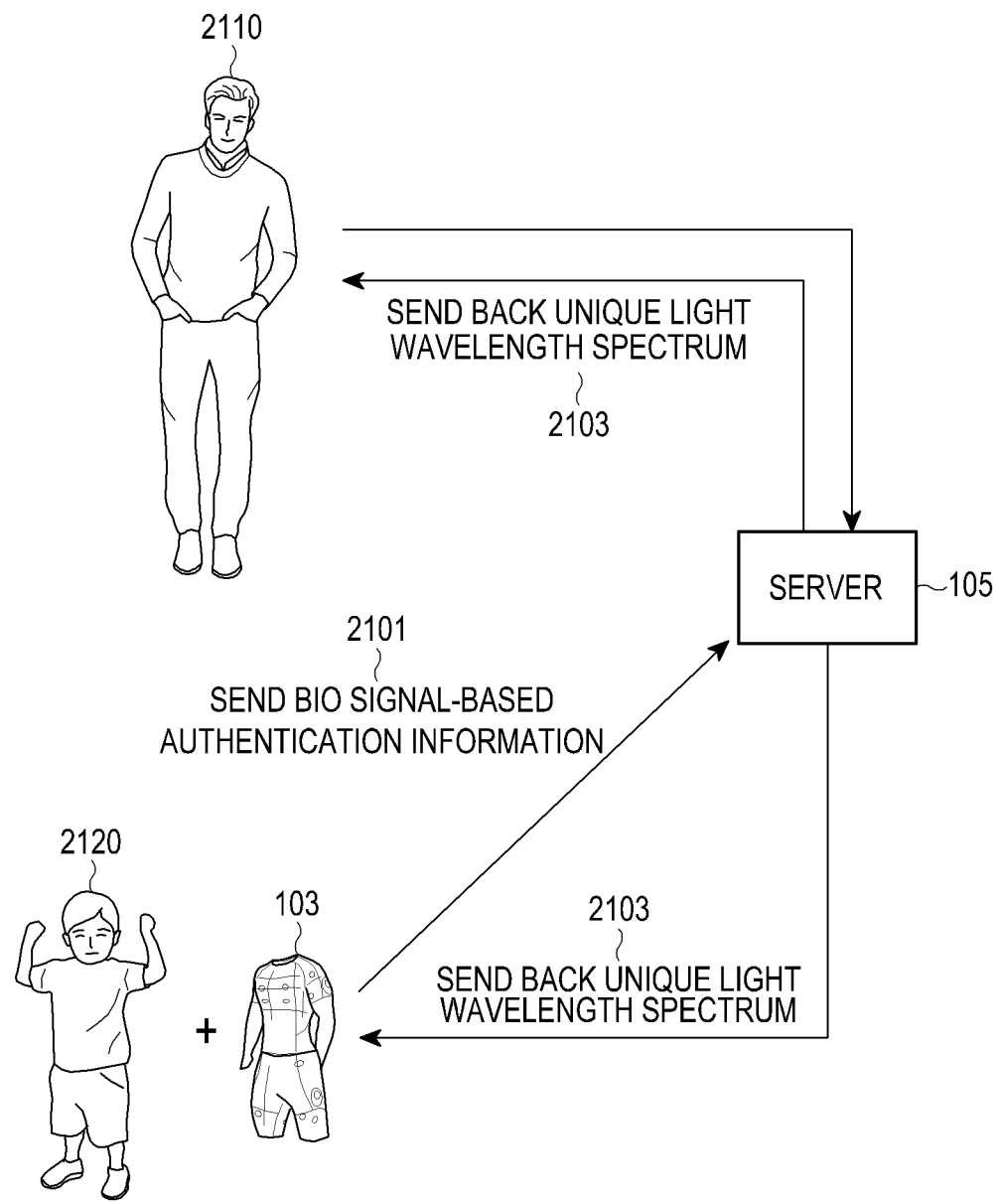

FIGS. 21A and 21B are diagrams illustrating other examples of providing a service in a wear system for providing services according to an example embodiment of the present disclosure. The service provision according to an example embodiment as illustrated in FIGS. 21A and 21B may be performed in the wear system 100 of FIG. 1, for example.

FIGS. 21A and 21B illustrate a find missing children service using the wear system.

Referring to FIG. 21A, in operation 2101, the parent 2110 may access the server 105 using a separate electronic device to generate identification information (e.g., GUID) regarding the child 2120, and while logging in the server through the electronic device, the server 105 may receive authentication information including a bio signal from the wear device 103 worn by the child 2120.

The server 105 may register the received authentication information to correspond to the identification information (e.g., GUID) regarding the child 2120, generate a unique key based on the authentication information, and generate a unique wavelength spectrum value using a Hash function based on the authentication information.

In operation 2103, the server 105 may transmit the unique key and the unique wavelength spectrum value to the electronic device of the parent 2110 and the wear device 103 worn by the child 2120.

The wear device 103 worn by the child 2120 may emit a light beam having the unique wavelength spectrum value using the unique key received from the server 105. The wear device 103 worn by the child 2120 may emit a light beam of a wavelength distinct from that of visible light.

The parent 2110 may sense the light beam emitted from the wear device 103 worn by the child 2120 through the electronic device equipped with a camera using the unique key. The display of the camera-equipped electronic device may display the light beam emitted from the wear device 103 with only the light beam highlighted, allowing the location of the child 2120 to be displayed projected in real life.

The camera included in the electronic device may generally sense 400 mm to 700 mm wavelengths among which 350 mm to 1000 mm wavelengths may be sensed as visible light, and 700 mm to 1000 mm wavelengths which are an infrared (IR) light spectrum may be sensed. A portion of the IR light spectrum may be allocated to sense the light emitted from the wear device 103.

Alternatively, the electronic device may come up with a separate device for sensing light emitted from the wear device 103.

As illustrated in (a) of FIG. 21B, an IR camera 2130 may be attached to the electronic device to sense light emitted from the wear device 103 worn by the child 2120.

Or, as illustrated in (b) of FIG. 21B, an external filter 2140 may be mounted on the camera of the electronic device to transmit visible light or IR rays. The external filter may have a part 2140a passing only visible light through and a part 2140b passing only IR light through. Accordingly, the part 2140a of the external filter 2140, which transmits only visible light, may normally be positioned corresponding to the camera of the electronic device while, upon sensing light emitted from the wear device 103, the part 2140b of the external filter 2140, which transmits only IR light, is positioned corresponding to the camera of the electronic device.

Figure 22:
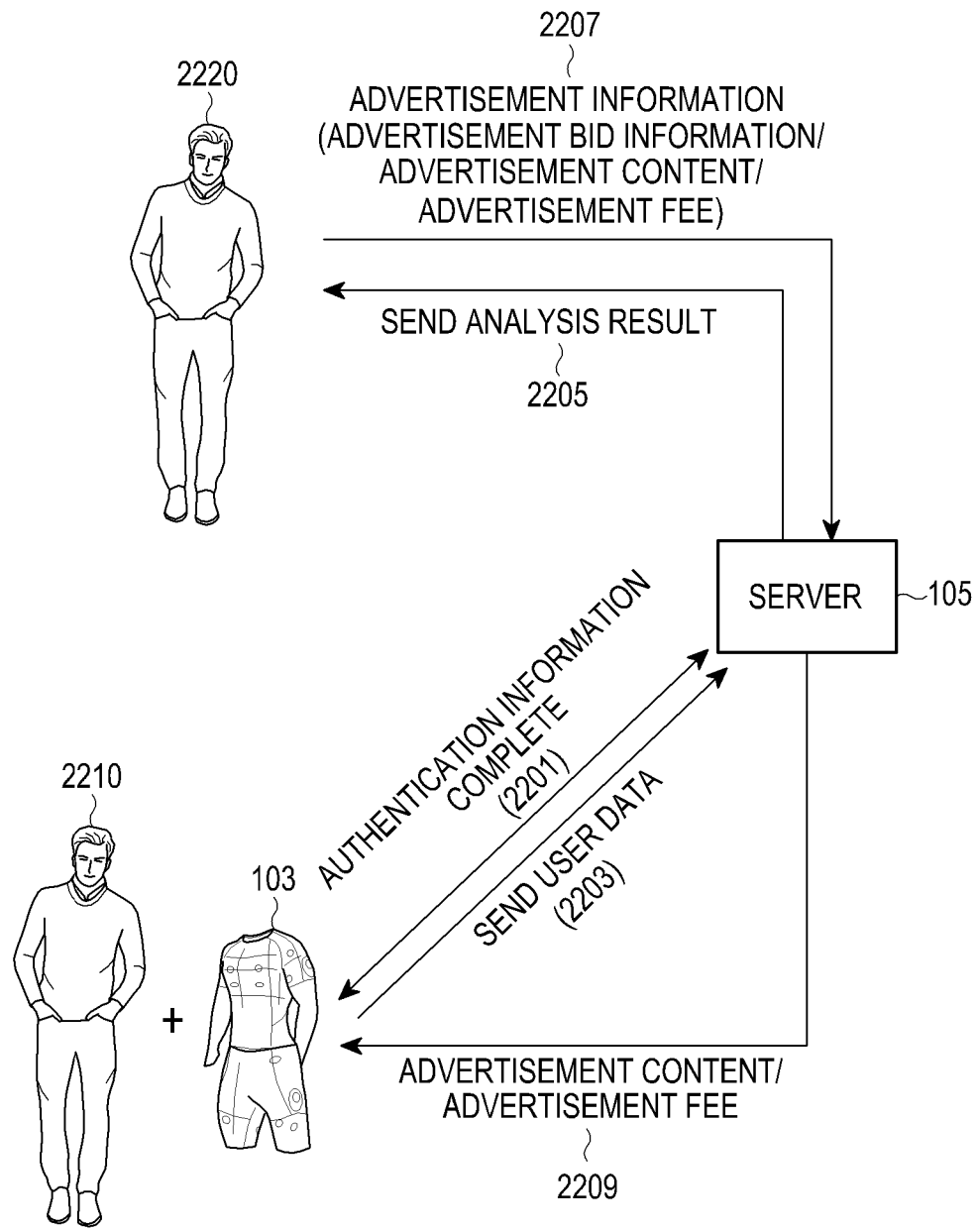
FIG. 22 is a diagram illustrating an example operation for providing an advertisement service in a wear system for providing services according to an example embodiment of the present disclosure.

FIG. 22 is a diagram illustrating an example operation for providing an advertisement service in a wear system for providing services according to an example embodiment of the present disclosure. The advertisement service providing operations according to an example embodiment as illustrated in FIG. 13 may be performed in the wear system 100 of FIG. 1, for example.

Referring to FIG. 22, the user 2210 wearing the wear device 103 is completely authenticated through the server in operation 2201, and the wear device 103 may transmit user data of the wear device 103 to the server 105 in operation 2203.

In operation 2205, the server 105 may generate a user profile based on user data gathered from the wear device 103 and store the generated user profile corresponding to identification information regarding the user.

Further, the server 105 may analyze the user profile stored corresponding to each of the plurality of identification information, analyze a per-area distribution and area-specific and profile change trend, and provide a result of the analysis to an application developer, service provider, or advertisement owner 2220.

In operation 2207, the advertisement owner 2220 may transmit, to the server 105 based on the received analysis result, advertisement information including profiles of users to which the advertisement is to be exposed, additional exposure conditions, such as profiles and areas, period during which the advertisement is to be exposed, advertisement contents, and advertisement fee.

In operation 2209, the server 105 may transmit the advertisement contents and advertisement fee to the wear device 103 worn by the user 2210 based on the advertisement information received from the advertisement owner.

The display of the wear device 103 worn by the user 2210 may output the advertisement content received from the advertisement owner 2220 through the server 105.

The user 2210 may access the server 105 through the smart wear device 103 or an electronic device connected via communication with the smart wear device 103 to identify a list of advertisements a request for which the user 2210 has received. Upon displaying the advertisement list, an exposure time and number of users meeting a condition per advertisement may be predicted, and an advertisement fee expected to be paid to the user may be displayed as well.

When the user 2210 accesses the server 105 and selects an advertisement desired to be exposed on his smart wear device 103, the server 105 may transmit the corresponding advertisement content, advertisement exposure period, and advertisement condition to the smart wear device 103 worn by the user 2210. The display of the smart wear device 103 may display an advertisement matching the advertisement exposure period and condition. When the display of the smart wear device 103 displays at least two advertisements, the advertisements may sequentially be exposed with certain time periods respectively allocated to the advertisements.

The server 105 may provide a dashboard to the advertisement owner, so that he may monitor, in real-time, exposure circumstances of advertisements registered (e.g., user count or aggregate total advertisement exposure time).

The advertisement owner 2220 may pay the server 105 a fee as per the advertisement exposure time, number of users to which the advertisement has been exposed, and exposure time differences.

The server 105 may pay the user to which the advertisement has been exposed for exposure of the advertisement based on a total sum of advertisement exposure times during the advertisement period per user after the advertisement period registered expires. An advertisement exposure payment a user may receive may be determined by Equation 1 below.

$$\text{Advertisement exposure payment to user } i = \frac{\text{Bid amount}}{\Sigma t_i} \times t_i \quad \text{[Equation 1]}$$

($t_i$ = Time period of advertisement exposure by user $i$)

The server 105 may take only the period during which the user 2210 wears the wear device 103 as the advertisement exposure time while excluding the time during which the display of the wear device 103 is hidden by, e.g., other clothes, from the advertisement exposure time.

The server 105 may detect the exposure of advertisement through the display of the wear device 103 by a sensor attached t the display, such as an illumination sensor or proximity sensor.

Figure 23:
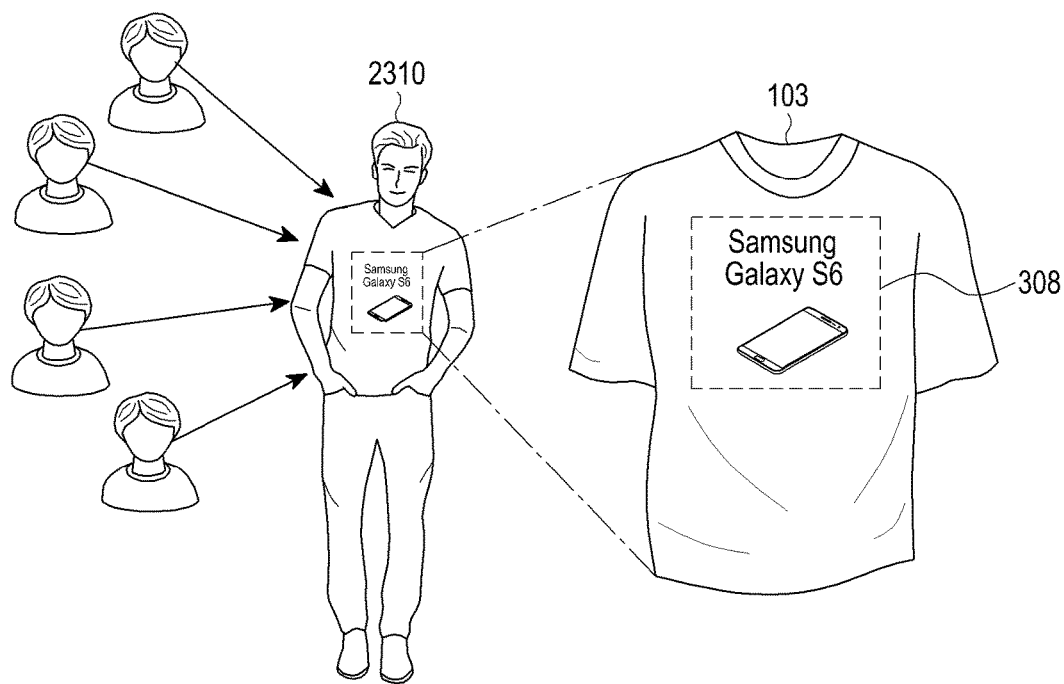
FIG. 23 is a diagram illustrating an example operation for exposing an advertisement service in a wear system for providing services according to an example embodiment of the present disclosure.

FIG. 23 is a diagram illustrating an example operation for exposing an advertisement service in a wear system for providing services according to an example embodiment of the present disclosure.

As illustrated in FIG. 23, when an advertisement content is output on the display 308 of the wear device 103 worn by the user 2310, the smart wear device 103 worn by each user may be utilized as an advertisement board, enhancing advertisement effects.

Further, when an advertisement content is output on the display 308 of the wear device 103 worn by the user 2310, the advertisement may be effectively exposed to adjacent people through the wear device 103 worn by the user.

Further, the advertisement owner may select the profile of a user who is to serve as an advertisement board and set up an advertisement exposure time and area and register the advertisement. The server may provide the number of users having the profile selected by the advertisement owner in real-time or at predetermined periods and reflect whether the wear device is worn and whether the advertisement is exposed to calculate advertisement fees.

According to an example embodiment of the present disclosure, a method for providing a service may comprise detecting authentication information regarding a user wearing a wear device in a first state and transmitting the authentication information to a server by the wear device, upon detecting the user's identification information using the authentication information received from the wear device, completing authentication of the user by the server, upon completing the authentication of the user through the server, detecting user data of the wear device in a second state and transmitting the user data to the server by the wear device, generating a user profile based on the user data received from the wear device, storing the user profile corresponding to the identification information by the server, and providing service information related to the user to the wear device by the server.

According to an example embodiment of the present disclosure, transmitting to the server may include detecting wearing the wear device using at least one sensor of a plurality of sensors in the first state which is a low-power, standby state by a first controller of the wear device and detecting the authentication information using the at least one sensor by the first controller of the wear device.

According to an example embodiment of the present disclosure, the at least one sensor of the plurality of sensors may detect a bio signal of the user wearing the wear device, and the authentication information may include the bio signal of the user.

According to an example embodiment of the present disclosure, transmitting the user data to the server may include, upon completing the authentication of the user through the server in the first state, waking up a second controller and allowing a first controller of the wear device to switch into a sleep state by the first controller of the wear device and detecting the user data of the wear device using a plurality of sensors in the second state and transmitting the user data to the server by the second controller of the wear device.

According to an example embodiment of the present disclosure, the method may further comprise, upon detecting taking off the wear device using at least one sensor of a plurality of sensors in the second state, waking up the first controller and allowing the second controller to switch into the sleep state by the second controller of the wear device.

According to an example embodiment of the present disclosure, an operation of authenticating the user through the server may be performed using an electronic device connected with the wear device, the user data may be transmitted to the server, and service information related to the user may be received from the server.

According to an example embodiment of the present disclosure, detecting the identification information may include detecting, by the server, identification information stored corresponding to the authentication information received from the wear device among a plurality of identification information stored in the server.

According to an example embodiment of the present disclosure, the method may further comprise accessing the server, generating identification information regarding the user, and accessing the server using the generated identification information by an electronic device, transmitting first authentication information detected using a first authentication sensor to the server from the wear device worn by the user, registering the first authentication information received from the wear device as new authentication information corresponding to the identification information by the server, transmitting second authentication information to the server using a second authentication sensor from another wear device worn by the user, and when the second authentication information received from the other wear device is not present as authentication information corresponding to the identification information, registering the second authentication information as additional authentication information corresponding to the identification information by the server.

According to an example embodiment of the present disclosure, the first authentication information and the second authentication information may represent different types of bio information.

According to an example embodiment of the present disclosure, the method may further comprise, upon completing the authentication of the user through the server, transmitting configuration information regarding the wear device to the server by the wear device and detecting service information corresponding to the configuration information regarding the wear device received from the wear device and transmitting the service information to the wear device by the server.

According to an example embodiment of the present disclosure, the service information corresponding to the configuration information regarding the wear device may include at least one application available on the wear device.

According to an example embodiment of the present disclosure, the method may further comprise, when not in communication connection with the server, storing the user data in the wear device or an electronic device connected via communication with the wear device and when establishing a communication connection with the server, transmitting the user data stored in the wear device or the electronic device to the server to be synced.

According to an example embodiment of the present disclosure, there is provided a storage medium recording a program including commands configured to, when executed by at least one processor, enable the at least one processor to perform at least one operation including detecting authentication information regarding a user wearing a wear device in a first state and transmitting the authentication information to a server by the wear device, upon detecting the user's identification information using the authentication information received from the wear device, completing authentication of the user by the server, upon completing the authentication of the user through the server, detecting user data of the wear device in a second state and transmitting the user data to the server by the wear device, generating a user profile based on the user data received from the wear device and storing the user profile corresponding to the identification information by the server, and providing service information related to the user to the wear device by the server.

What is claimed is:

1. A wear device comprising:
   a communication module comprising communication circuitry; and
   a first controller configured to:
      detect authentication information regarding a user wearing the wear device in a first state which is a low-power standby state,
      transmit, through the communication module, the authentication information to a server,
      receive, through the communication module, authentication complete information generated based on the authentication information and identification information regarding the user from the server, and
      wake up a second controller and switch into a sleep state in response to the receiving the authentication complete information,
   the second controller configured to:
      after being woken up by the first controller, detect user data of the wear device in a second state, and transmit the user data to the server.

2. The wear device of claim 1,
   wherein the first controller is configured to detect the authentication information and wearing of the wear device using at least one sensor among a plurality of sensors in the first state;
   wherein the second controller in the second state is configured to detect the user data of the wear device using the plurality of sensors, upon detecting taking off the wear device using the at least one sensor, wake up the first controller and switching into the sleep state;
   wherein the plurality of sensors is configured to detect the wearing and taking off the wear device, the authentication information, and the user data.

3. The wear device of claim 2, wherein the at least one sensor of the plurality of sensors is configured to detect a bio signal of the user wearing the wear device, and wherein the authentication information includes the bio signal.

4. The wear device of claim 1, wherein the first controller is further configured to:
   perform an operation of authenticating the user through the server using an electronic device connected with the wear device,
   transmit the user data to the server, and
   receive service information related to the user from the server.

5. The wear device of claim 1, wherein the second controller is further configured to:
   transmit configuration information regarding the wear device to the server upon completing the authentication of the user through the server, and
   receive service information corresponding to the configuration information regarding the wear device from the server,
   wherein the service information corresponding to the configuration information regarding the wear device includes at least one application available on the wear device.

6. The wear device of claim 1, wherein the second controller is further configured to:
   store the user data in the wear device or an electronic device connected via the communication module if the wear device has not established a communication connection with the server, and
   transmit the user data stored in the wear device or the electronic device to the server to be synced if a communication connection with the server is established.

7. A method comprising:
   detecting authentication information regarding a user wearing a wear device in a first state which is a low-power standby state;
   transmitting the authentication information to a server;
   receiving authentication complete information generated based on the authentication information and identification information regarding the user from the server;
   waking up a second controller and switching a first controller into a sleep state in response to the receiving the authentication complete information;
   after the second controller wakes up, the second controller detecting user data of the wear device in a second state, and
   transmitting the user data to the server.

8. The method of claim 7, wherein transmitting to the server includes detecting, by a first controller of the wear device, wearing the wear device using at least one sensor of a plurality of sensors in the first state, and detecting, by the first controller of the wear device, the authentication information using the at least one sensor.

9. The method of claim 8, wherein the at least one sensor of the plurality of sensors detects a bio signal of the user wearing the wear device, and wherein the authentication information includes the bio signal of the user.

10. The method of claim 7, further comprising: allowing the first controller of the wear device to switch into a sleep state and detecting the user data of the wear device using a plurality of sensors in the second state and transmitting the user data to the server by the second controller of the wear device.

11. The method of claim 7, further comprising, waking up the first controller and switching the second controller into the sleep state upon detecting taking off the wear device using at least one sensor of a plurality of sensors in the second state.

12. The method of claim 7, further comprising:
   transmitting configuration information regarding the wear device to the server upon completing the authentication of the user through the server; and
   wherein the service information corresponding to the configuration information regarding the wear device includes at least one application available on the wear device.

13. The method of claim 7, further comprising:
   storing the user data in the wear device or an electronic device connected via communication with the wear device if the wear device is not in communication with the server; and
   transmitting the user data stored in the wear device or the electronic device to the server to be synced if a communication connection with the server is established.

* * * * *